(12) United States Patent
Dlugos, Jr. et al.

(10) Patent No.: US 8,114,345 B2
(45) Date of Patent: Feb. 14, 2012

(54) SYSTEM AND METHOD OF STERILIZING AN IMPLANTABLE MEDICAL DEVICE

(75) Inventors: Daniel F. Dlugos, Jr., Middletown, OH (US); Mark S. Ortiz, Milford, OH (US); David N. Plescia, Cincinnati, OH (US); Mark Leuenberger, Loveland, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 943 days.

(21) Appl. No.: 12/028,344

(22) Filed: Feb. 8, 2008

(65) Prior Publication Data

US 2009/0202387 A1 Aug. 13, 2009

(51) Int. Cl.
*A61L 2/00* (2006.01)
*A61B 17/08* (2006.01)
*A61N 1/00* (2006.01)

(52) U.S. Cl. .............. 422/22; 606/157; 607/60
(58) Field of Classification Search .............. 422/22; 606/157; 607/60
See application file for complete search history.

(56) References Cited

U.S. PATENT DOCUMENTS

| | | | |
|---|---|---|---|
| RE3,036 E | 7/1868 | Shunk |
| RE3,037 E | 7/1868 | Tucker |
| RE3,115 E | 9/1868 | Lewis |
| RE3,187 E | 11/1868 | Winchester |
| RE3,322 E | 3/1869 | Murch |
| 236,373 A | 1/1881 | Spilman |
| 322,388 A | 7/1885 | Lord |
| 400,401 A | 3/1889 | Gutzkow |
| D23,637 S | 9/1894 | Casad et al. |
| D24,900 S | 11/1895 | Clemecet |
| D25,318 S | 3/1896 | Perky |

(Continued)

FOREIGN PATENT DOCUMENTS

CA 1059035 7/1979

(Continued)

OTHER PUBLICATIONS

"Application Specific Integrated Circuits (ASICs)", Honeywell product information from website http://www.honeywell.com/sites/portal?smap=aerospace&page=Radiation-Hardened-Electronics3&theme=T18&catID=CE06BEF88-65F8-6A1E-4ED1-6A1EC1B7AE7A&id=HA0E380D3-C27B-9EBF-AAC8-9FAF8851256D&sel=1&sel4=1; 1 page.

(Continued)

*Primary Examiner* — Kevin Joyner
(74) *Attorney, Agent, or Firm* — Nutter McClennen & Fish LLP

(57) ABSTRACT

An implantable system having internal circuitry configured to withstand a pre-determined amount of sterilization radiation is provided. In general, the system includes an internal control module in electrical communication with an implantable medical device. The internal control module can include a circuit board configured to withstand radiation and/or any number of integrated circuits (e.g., application specific integrated circuits) wherein the circuits or at least some portion thereof are fabricated so as to withstand some amount of radiation. For example, some portion of the circuitry can be fabricated utilizing radiation compliant material(s), silicon-on-insulator technology, and/or gallium arsenide technology. Additionally, the circuitry can include various components which are inherently resistant to such radiation (e.g., components fabricated utilizing magnetic field based technology, surface acoustical wave devices, etc.). A method of sterilizing an implantable medical device via radiation is also provided.

13 Claims, 11 Drawing Sheets

U.S. PATENT DOCUMENTS

| | | |
|---|---|---|
| D27,151 S | 6/1897 | Moulten |
| D29,715 S | 11/1898 | Wheeler |
| D29,745 S | 11/1898 | Bunker |
| D29,885 S | 12/1898 | Gillespie et al. |
| D30,690 S | 5/1899 | Schwedtmann |
| D30,966 S | 6/1899 | Howe |
| D31,230 S | 7/1899 | Hogan |
| 689,758 A | 12/1901 | Shaw |
| 724,913 A | 4/1902 | Montgomery |
| 899,477 A | 9/1908 | Williams |
| 926,197 A | 6/1909 | Kim |
| 953,875 A | 4/1910 | Waring |
| 991,192 A | 5/1911 | Battenfeld |
| 1,087,988 A | 2/1914 | Sheldon |
| 1,210,701 A | 1/1917 | Ryden |
| 1,219,296 A | 3/1917 | Hahn |
| 1,224,355 A | 5/1917 | Brown |
| 1,263,914 A | 4/1918 | Martin |
| 1,310,290 A | 7/1919 | Piechowicz |
| 1,384,873 A | 7/1921 | Strickland |
| 1,421,507 A | 7/1922 | Lindberg |
| 1,551,525 A | 8/1925 | Hamer |
| 1,560,973 A | 11/1925 | Cheron |
| 1,620,633 A | 3/1927 | Colvin |
| 1,623,403 A | 4/1927 | Friel |
| 1,689,085 A | 10/1928 | Russell et al. |
| 1,764,071 A | 6/1930 | Foulke |
| 1,782,704 A | 11/1930 | Woodruff |
| 1,807,107 A | 5/1931 | Sternberch |
| 1,865,446 A | 7/1932 | Sears |
| 1,882,338 A | 10/1932 | Reed et al. |
| 1,924,781 A | 8/1933 | Gaiser |
| 2,027,875 A | 1/1936 | Odend'hal |
| 2,063,430 A | 12/1936 | Graser |
| 2,099,160 A | 11/1937 | Charch |
| 2,105,127 A | 1/1938 | Petrone |
| 2,106,192 A | 1/1938 | Saville |
| 2,143,429 A | 1/1939 | Auble |
| 2,166,603 A | 7/1939 | Menzer |
| 2,168,427 A | 8/1939 | McConkey |
| 2,174,525 A | 10/1939 | Padernal |
| 2,177,564 A | 10/1939 | Havill |
| 2,178,463 A | 10/1939 | Bahnson |
| 2,180,599 A | 11/1939 | Menasco |
| 2,203,460 A | 6/1940 | Fieber |
| 2,206,038 A | 7/1940 | Ford |
| 2,216,374 A | 10/1940 | Martin |
| 2,223,699 A | 12/1940 | Norgren |
| 2,225,145 A | 12/1940 | Baumbach |
| 2,225,880 A | 12/1940 | Montelius |
| 2,261,060 A | 10/1941 | Giesler |
| 2,261,355 A | 11/1941 | Flynn |
| 2,295,539 A | 9/1942 | Beach |
| 2,303,108 A | 11/1942 | Blackburn |
| 2,303,502 A | 12/1942 | Rous |
| 2,318,819 A | 5/1943 | Verson |
| 2,327,407 A | 8/1943 | Edyvean |
| 2,327,615 A | 8/1943 | Ankarlo |
| 2,354,571 A | 7/1944 | Blain |
| 2,426,392 A | 8/1947 | Fennema |
| 2,426,817 A | 9/1947 | Charlton et al. |
| 2,440,260 A | 4/1948 | Gall |
| 2,442,573 A | 6/1948 | Stafford |
| 2,453,217 A | 11/1948 | Gregg et al. |
| 2,455,859 A | 12/1948 | Foley |
| 2,477,922 A | 8/1949 | Emery et al. |
| 2,478,876 A | 8/1949 | Nelson |
| 2,482,392 A | 9/1949 | Whitaker |
| 2,494,881 A | 1/1950 | Kost |
| 2,509,210 A | 5/1950 | Clark |
| 2,509,673 A | 5/1950 | Church |
| 2,511,765 A | 6/1950 | Bradbury |
| 2,520,056 A | 8/1950 | Pozun |
| 2,521,976 A | 9/1950 | Hays |
| 2,533,924 A | 12/1950 | Foley |
| 2,538,259 A | 1/1951 | Merriman |
| 2,581,479 A | 1/1952 | Grashman |
| 2,600,324 A | 6/1952 | Rappaport |
| 2,606,003 A | 8/1952 | McNeill |
| 2,615,940 A | 10/1952 | Williams |
| 2,632,447 A | 3/1953 | Dobes |
| 2,639,342 A | 5/1953 | Cope |
| 2,640,119 A | 5/1953 | Bradford, Jr. |
| 2,641,742 A | 6/1953 | Wolfe |
| 2,651,304 A | 9/1953 | Browner |
| 2,665,577 A | 1/1954 | Sanowskis |
| 2,673,999 A | 4/1954 | Shey |
| 2,676,609 A | 4/1954 | Pfarrer |
| 2,684,118 A | 7/1954 | Osmun |
| 2,689,611 A | 9/1954 | Martinson |
| 2,697,435 A | 12/1954 | Ray |
| 2,723,323 A | 11/1955 | Niemi |
| 2,734,992 A | 2/1956 | Elliot et al. |
| 2,740,007 A | 3/1956 | Amelang |
| 2,740,853 A | 4/1956 | Hatman, Jr. |
| 2,742,323 A | 4/1956 | Shey |
| 2,747,332 A | 5/1956 | Morehouse |
| 2,753,876 A | 7/1956 | Kurt |
| 2,756,883 A | 7/1956 | Schreck |
| 2,756,983 A | 7/1956 | Furcini |
| 2,761,603 A | 9/1956 | Fairchild |
| 2,773,312 A | 12/1956 | Peck |
| 2,783,728 A | 3/1957 | Hoffmann |
| 2,787,875 A | 4/1957 | Johnson |
| 2,793,379 A | 5/1957 | Moore |
| 2,795,460 A | 6/1957 | Bletcher |
| 2,804,514 A | 8/1957 | Peters |
| 2,822,113 A | 2/1958 | Joiner, Jr. |
| 2,831,478 A | 4/1958 | Uddenberg et al. |
| 2,864,393 A | 12/1958 | Drake |
| 2,865,541 A | 12/1958 | Hicks |
| 2,870,024 A | 1/1959 | Martin |
| 2,883,995 A | 4/1959 | Bialous et al. |
| 2,886,355 A | 5/1959 | Wurzel |
| 2,895,215 A | 7/1959 | Neher et al. |
| 2,899,493 A | 8/1959 | Levine |
| 2,902,861 A | 9/1959 | Frost et al. |
| 2,923,531 A | 2/1960 | Bauer et al. |
| 2,924,263 A | 2/1960 | Landis |
| 2,924,432 A | 2/1960 | Arps et al. |
| 2,930,170 A | 3/1960 | Holsman et al. |
| 2,938,592 A | 5/1960 | Charske et al. |
| 2,941,338 A | 6/1960 | Santschi |
| 2,943,682 A | 7/1960 | Ingram, Jr. et al. |
| 2,958,781 A | 11/1960 | Marchal et al. |
| 2,961,479 A | 11/1960 | Bertling |
| 2,976,355 A | 3/1961 | Levine |
| 2,976,686 A | 3/1961 | Stelzer |
| 2,977,876 A | 4/1961 | Meyers |
| 2,986,715 A | 5/1961 | Church et al. |
| 2,989,019 A | 6/1961 | Van Sciver, II |
| 3,010,692 A | 11/1961 | Jentoft |
| 3,013,234 A | 12/1961 | Bourns |
| 3,018,791 A | 1/1962 | Knox |
| 3,034,356 A | 5/1962 | Bieganski |
| 3,040,800 A | 6/1962 | Hartley |
| 3,054,618 A | 9/1962 | Abrams et al. |
| 3,060,262 A | 10/1962 | Hoer |
| 3,070,373 A | 12/1962 | Mathews et al. |
| 3,082,414 A | 3/1963 | Papaminas |
| 3,085,577 A | 4/1963 | Berman et al. |
| 3,096,410 A | 7/1963 | Anderson |
| 3,099,262 A | 7/1963 | Bigliano |
| 3,125,028 A | 3/1964 | Rohde |
| 3,126,029 A | 3/1964 | Englesson |
| 3,129,072 A | 4/1964 | Cook et al. |
| 3,135,914 A | 6/1964 | Callan et al. |
| 3,144,017 A | 8/1964 | Muth |
| 3,151,258 A | 9/1964 | Sonderegger et al. |
| 3,153,460 A | 10/1964 | Raskin |
| 3,161,051 A | 12/1964 | Perry, Jr. |
| 3,167,044 A | 1/1965 | Henrickson |
| 3,171,549 A | 3/1965 | Orloff |
| 3,172,700 A | 3/1965 | Haas |
| 3,173,269 A | 3/1965 | Imbertson |
| 3,182,494 A | 5/1965 | Beatty et al. |
| 3,187,181 A | 6/1965 | Keller |

| | | | | | | |
|---|---|---|---|---|---|---|
| 3,187,745 A | 6/1965 | Baum et al. | | 3,482,816 A | 12/1969 | Arnold |
| 3,190,388 A | 6/1965 | Moser et al. | | 3,487,959 A | 1/1970 | Pearne at al. |
| 3,205,547 A | 9/1965 | Riekse | | 3,491,842 A | 1/1970 | Delacour et al. |
| 3,208,255 A | 9/1965 | Burk | | 3,492,638 A | 1/1970 | Lane |
| 3,209,570 A | 10/1965 | Hills | | 3,502,829 A | 3/1970 | Reynolds |
| 3,221,468 A | 12/1965 | Casey | | 3,503,116 A | 3/1970 | Strack |
| 3,228,703 A | 1/1966 | Wilson | | 3,504,664 A | 4/1970 | Haddad |
| 3,229,684 A | 1/1966 | Nagumo et al. | | 3,505,808 A | 4/1970 | Eschle |
| 3,236,088 A | 2/1966 | Moller | | 3,509,754 A | 5/1970 | Massingill et al. |
| 3,238,624 A | 3/1966 | McCabe | | 3,512,517 A | 5/1970 | Kadish et al. |
| 3,240,510 A | 3/1966 | Spouge | | 3,514,919 A | 6/1970 | Ashton et al. |
| 3,245,642 A | 4/1966 | Dicke | | 3,516,220 A | 6/1970 | Buford et al. |
| 3,255,568 A | 6/1966 | Martin et al. | | 3,517,553 A | 6/1970 | Williams et al. |
| 3,260,091 A | 7/1966 | Shaw, Jr. | | 3,527,226 A | 9/1970 | Hakin et al. |
| 3,265,822 A | 8/1966 | Moulten | | 3,529,908 A | 9/1970 | Smith |
| 3,266,487 A | 8/1966 | Watkins et al. | | 3,530,449 A | 9/1970 | Anderson |
| 3,273,447 A | 9/1966 | Frank | | 3,533,403 A | 10/1970 | Woodson |
| 3,283,352 A | 11/1966 | Hu | | 3,534,728 A | 10/1970 | Barrows |
| 3,290,919 A | 12/1966 | Malinak et al. | | 3,534,872 A | 10/1970 | Roth et al. |
| 3,292,493 A | 12/1966 | Franklin | | 3,535,914 A | 10/1970 | Veith et al. |
| 3,292,888 A | 12/1966 | Fischer | | 3,539,009 A | 11/1970 | Kudlaty |
| 3,294,988 A | 12/1966 | Packard | | 3,543,744 A | 12/1970 | LePar |
| 3,299,603 A | 1/1967 | Shaw | | 3,545,275 A | 12/1970 | Harrison et al. |
| 3,299,882 A | 1/1967 | Masino | | 3,550,583 A | 12/1970 | Chiku |
| 3,301,514 A | 1/1967 | Sugaya | | 3,550,847 A | 12/1970 | Scott |
| 3,302,457 A | 2/1967 | Mayes | | 3,563,094 A | 2/1971 | Rieschel |
| 3,306,384 A | 2/1967 | Ross | | 3,563,245 A | 2/1971 | McLean et al. |
| 3,313,314 A | 4/1967 | Burke et al. | | 3,566,083 A | 2/1971 | McMillin |
| 3,316,935 A | 5/1967 | Kaiser et al. | | 3,566,875 A | 3/1971 | Stoehr |
| 3,320,750 A | 5/1967 | Haise et al. | | 3,568,367 A | 3/1971 | Myers |
| 3,321,035 A | 5/1967 | Tarpley | | 3,568,636 A | 3/1971 | Lockwood |
| 3,332,788 A | 7/1967 | Barnby | | 3,576,554 A | 4/1971 | Temps, Jr. et al. |
| 3,334,510 A | 8/1967 | Hallesy | | 3,580,082 A | 5/1971 | Strack |
| 3,339,401 A | 9/1967 | Peters | | 3,581,402 A | 6/1971 | London et al. |
| 3,340,868 A | 9/1967 | Darling | | 3,583,387 A | 6/1971 | Garner et al. |
| 3,347,162 A | 10/1967 | Braznell | | 3,587,204 A | 6/1971 | George |
| 3,350,944 A | 11/1967 | De Michele | | 3,590,809 A | 7/1971 | London |
| 3,353,364 A | 11/1967 | Blanding | | 3,590,818 A | 7/1971 | Lemole |
| 3,353,481 A | 11/1967 | Antonucci | | 3,590,992 A | 7/1971 | Soderstrom et al. |
| 3,356,334 A | 12/1967 | Scaramucci | | 3,592,183 A | 7/1971 | Watkins et al. |
| 3,356,510 A | 12/1967 | Barnby | | 3,594,519 A | 7/1971 | Schmidlin |
| 3,357,218 A | 12/1967 | Mitchell | | 3,602,885 A | 8/1971 | Grajeda |
| 3,357,461 A | 12/1967 | Friendship | | 3,610,016 A | 10/1971 | Bultman |
| 3,359,741 A | 12/1967 | Nelson | | 3,610,851 A | 10/1971 | Krupski |
| 3,361,300 A | 1/1968 | Kaplan | | 3,611,811 A | 10/1971 | Lissau |
| 3,364,929 A | 1/1968 | Ide et al. | | 3,614,926 A | 10/1971 | Brechtel |
| 3,365,684 A | 1/1968 | Stemke | | 3,614,955 A | 10/1971 | Mirowski et al. |
| 3,378,456 A | 4/1968 | Roberts | | 3,619,742 A | 11/1971 | Rud, Jr. |
| 3,380,445 A | 4/1968 | Frasier | | 3,623,371 A | 11/1971 | Jullien-Davin |
| 3,380,649 A | 4/1968 | Roberts | | 3,624,854 A | 12/1971 | Strong |
| 3,385,022 A | 5/1968 | Anderson | | 3,630,242 A | 12/1971 | Schieser et al. |
| 3,389,355 A | 6/1968 | Schroeder, Jr. | | 3,631,847 A | 1/1972 | Hobbs, II |
| 3,393,612 A | 7/1968 | Gorgens at al. | | 3,633,881 A | 1/1972 | Yurdin |
| 3,396,561 A | 8/1968 | Day | | 3,635,061 A | 1/1972 | Rydell et al. |
| 3,399,667 A | 9/1968 | Nishimoto et al. | | 3,635,074 A | 1/1972 | Moos et al. |
| 3,400,734 A | 9/1968 | Rosenberg | | 3,638,496 A | 2/1972 | King |
| 3,403,237 A | 9/1968 | Wysong | | 3,644,883 A | 2/1972 | Borman et al. |
| 3,409,924 A | 11/1968 | Slama | | 3,648,687 A | 3/1972 | Ramsey, III |
| 3,411,347 A | 11/1968 | Wirth at al. | | 3,651,289 A | 3/1972 | Nagashima et al. |
| 3,417,476 A | 12/1968 | Martens | | 3,651,405 A | 3/1972 | Whitney et al. |
| 3,420,325 A | 1/1969 | McAlister et al. | | 3,653,671 A | 4/1972 | Shipes |
| 3,422,324 A | 1/1969 | Webb | | 3,659,615 A | 5/1972 | Enger |
| 3,426,165 A | 2/1969 | Beaman | | 3,677,685 A | 7/1972 | Aoki et al. |
| 3,438,391 A | 4/1969 | Yocum | | 3,686,958 A | 8/1972 | Porter et al. |
| 3,443,608 A | 5/1969 | Copping et al. | | 3,688,568 A | 9/1972 | Karper et al. |
| 3,445,335 A | 5/1969 | Gluntz | | 3,701,392 A | 10/1972 | Wirth et al. |
| 3,447,281 A | 6/1969 | Bufford et al. | | 3,702,677 A | 11/1972 | Heffington |
| 3,450,153 A | 6/1969 | Hildebrandt et al. | | 3,703,099 A | 11/1972 | Rouse et al. |
| 3,453,546 A | 7/1969 | Fryer | | 3,712,138 A | 1/1973 | Alinari et al. |
| 3,453,848 A | 7/1969 | Williamson | | 3,713,124 A | 1/1973 | Durland et al. |
| 3,456,134 A | 7/1969 | Ko | | 3,719,524 A | 3/1973 | Ripley et al. |
| 3,457,909 A | 7/1969 | Laird | | 3,721,412 A | 3/1973 | Kindorf |
| 3,460,557 A | 8/1969 | Gallant | | 3,723,247 A | 3/1973 | Leine et al. |
| 3,463,338 A | 8/1969 | Schneider | | 3,724,000 A | 4/1973 | Eakman |
| 3,469,818 A | 9/1969 | Cowan | | 3,727,463 A | 4/1973 | Intraub |
| 3,470,725 A | 10/1969 | Brown et al. | | 3,727,616 A | 4/1973 | Lenzkes |
| 3,472,230 A | 10/1969 | Fogarty | | 3,730,174 A | 5/1973 | Madison |
| 3,478,344 A | 11/1969 | Schwitzgebel et al. | | 3,730,560 A | 5/1973 | Abildgaard et al. |
| 3,482,449 A | 12/1969 | Werner | | 3,731,679 A | 5/1973 | Wilhelmson et al. |

| | | |
|---|---|---|
| 3,731,681 A | 5/1973 | Blackshear et al. |
| 3,732,731 A | 5/1973 | Fussell, Jr. |
| 3,735,040 A | 5/1973 | Punt et al. |
| 3,736,930 A | 6/1973 | Georgi |
| 3,738,356 A | 6/1973 | Workman |
| 3,740,921 A | 6/1973 | Meyer et al. |
| 3,746,111 A | 7/1973 | Berthiaume et al. |
| 3,748,678 A | 7/1973 | Ballou |
| 3,749,098 A | 7/1973 | De Bennetot et al. |
| 3,749,422 A | 7/1973 | Abildgaard et al. |
| 3,749,423 A | 7/1973 | Abildgaard et al. |
| 3,750,194 A | 8/1973 | Summers |
| 3,757,770 A | 9/1973 | Brayshaw et al. |
| 3,759,095 A | 9/1973 | Short, Jr. et al. |
| 3,760,638 A | 9/1973 | Lawson et al. |
| 3,763,960 A | 10/1973 | John et al. |
| 3,765,142 A | 10/1973 | Lindquist et al. |
| 3,765,494 A | 10/1973 | Kielman, Jr. |
| 3,769,156 A | 10/1973 | Brecy et al. |
| 3,769,830 A | 11/1973 | Porter et al. |
| 3,774,243 A | 11/1973 | Ng et al. |
| 3,776,333 A | 12/1973 | Mathauser |
| 3,778,051 A | 12/1973 | Allen et al. |
| 3,780,578 A | 12/1973 | Sellman et al. |
| 3,781,902 A | 12/1973 | Shim et al. |
| 3,783,585 A | 1/1974 | Hoyland et al. |
| 3,789,667 A | 2/1974 | Porter et al. |
| 3,796,095 A | 3/1974 | Fussell, Jr. |
| 3,807,219 A | 4/1974 | Wallskog |
| 3,811,429 A | 5/1974 | Fletcher et al. |
| 3,815,722 A | 6/1974 | Sessoms |
| 3,818,765 A | 6/1974 | Eriksen et al. |
| 3,820,400 A | 6/1974 | Russo |
| 3,820,795 A | 6/1974 | Taylor |
| 3,823,610 A | 7/1974 | Fussell, Jr. |
| 3,825,065 A | 7/1974 | Lloyd et al. |
| 3,825,963 A | 7/1974 | Abildgaard et al. |
| 3,825,964 A | 7/1974 | Groswith, III et al. |
| 3,828,672 A | 8/1974 | Gazzola et al. |
| 3,828,766 A | 8/1974 | Krasnow |
| 3,831,588 A | 8/1974 | Rindner |
| 3,831,942 A | 8/1974 | Del Mar |
| 3,833,238 A | 9/1974 | Liard et al. |
| 3,834,167 A | 9/1974 | Tabor |
| 3,834,739 A | 9/1974 | Abildgaard et al. |
| 3,835,523 A | 9/1974 | Stansfield et al. |
| 3,839,708 A | 10/1974 | Bredesen et al. |
| 3,842,483 A | 10/1974 | Cramer |
| 3,842,668 A | 10/1974 | Lippke et al. |
| 3,845,664 A | 11/1974 | Perry, Jr. |
| 3,845,751 A | 11/1974 | Runstetler |
| 3,845,757 A | 11/1974 | Weyer |
| 3,847,434 A | 11/1974 | Weman et al. |
| 3,850,208 A | 11/1974 | Hamilton |
| 3,853,117 A | 12/1974 | Murr |
| 3,854,469 A | 12/1974 | Giori et al. |
| 3,855,902 A | 12/1974 | Kirst et al. |
| 3,857,399 A | 12/1974 | Zacouto et al. |
| 3,857,452 A | 12/1974 | Hartman |
| 3,857,745 A | 12/1974 | Grausch et al. |
| 3,858,581 A | 1/1975 | Kamen |
| 3,863,622 A | 2/1975 | Buuck |
| 3,863,933 A | 2/1975 | Tredway |
| 3,867,950 A | 2/1975 | Fischell |
| 3,868,008 A | 2/1975 | Brumbaugh |
| 3,868,679 A | 2/1975 | Arneson |
| 3,871,599 A | 3/1975 | Takada et al. |
| 3,872,285 A | 3/1975 | Shum et al. |
| 3,874,388 A | 4/1975 | King et al. |
| 3,876,980 A | 4/1975 | Haemmig et al. |
| 3,878,908 A | 4/1975 | Andersson et al. |
| 3,881,528 A | 5/1975 | Mackenzie |
| 3,893,111 A | 7/1975 | Cotter |
| 3,893,451 A | 7/1975 | Durand et al. |
| 3,895,681 A | 7/1975 | Griffin et al. |
| 3,899,862 A | 8/1975 | Muys et al. |
| 3,904,234 A | 9/1975 | Hill et al. |
| 3,908,334 A | 9/1975 | Rychiger et al. |
| 3,908,461 A | 9/1975 | Turpen |
| 3,908,721 A | 9/1975 | McGahey et al. |
| 3,910,087 A | 10/1975 | Jones |
| 3,912,168 A | 10/1975 | Mullins et al. |
| 3,912,304 A | 10/1975 | Abildgaard et al. |
| 3,918,286 A | 11/1975 | Whitehead |
| 3,918,291 A | 11/1975 | Pauly et al. |
| 3,920,965 A | 11/1975 | Sohrwardy et al. |
| 3,921,682 A | 11/1975 | McGahey et al. |
| 3,922,951 A | 12/1975 | Linsinger et al. |
| 3,923,060 A | 12/1975 | Ellinwood, Jr. |
| 3,924,635 A | 12/1975 | Hakim et al. |
| 3,928,980 A | 12/1975 | Ganzinotti et al. |
| 3,929,175 A | 12/1975 | Coone |
| 3,930,682 A | 1/1976 | Booth |
| 3,930,852 A | 1/1976 | Tanaka et al. |
| 3,936,028 A | 2/1976 | Norton et al. |
| 3,940,122 A | 2/1976 | Janzen et al. |
| 3,940,630 A | 2/1976 | Bergonz |
| 3,942,299 A | 3/1976 | Bory et al. |
| 3,942,382 A | 3/1976 | Hok et al. |
| 3,942,516 A | 3/1976 | Glynn et al. |
| 3,942,536 A | 3/1976 | Mirowski et al. |
| 3,943,915 A | 3/1976 | Severson |
| 3,945,704 A | 3/1976 | Kraus et al. |
| 3,946,613 A | 3/1976 | Silver |
| 3,946,615 A | 3/1976 | Hluchan |
| 3,946,724 A | 3/1976 | La Balme et al. |
| 3,948,141 A | 4/1976 | Shinjo et al. |
| 3,949,388 A | 4/1976 | Fuller |
| 3,953,289 A | 4/1976 | Costes et al. |
| 3,954,271 A | 5/1976 | Tredway, Sr. |
| 3,958,558 A | 5/1976 | Dunphy et al. |
| 3,961,425 A | 6/1976 | Swanson et al. |
| 3,961,646 A | 6/1976 | Schon et al. |
| 3,962,895 A | 6/1976 | Rydell et al. |
| 3,962,921 A | 6/1976 | Lips |
| 3,963,019 A | 6/1976 | Quandt |
| 3,964,485 A | 6/1976 | Neumeier |
| 3,964,770 A | 6/1976 | Abildgaard et al. |
| 3,967,737 A | 7/1976 | Peralta et al. |
| 3,968,473 A | 7/1976 | Patton et al. |
| 3,968,694 A | 7/1976 | Clark |
| 3,972,320 A | 8/1976 | Kalman |
| 3,973,753 A | 8/1976 | Wheeler |
| 3,973,858 A | 8/1976 | Poisson et al. |
| 3,974,655 A | 8/1976 | Halpern et al. |
| 3,974,865 A | 8/1976 | Fenton et al. |
| 3,977,391 A | 8/1976 | Fleischmann |
| 3,980,871 A | 9/1976 | Lindstrom et al. |
| 3,982,571 A | 9/1976 | Fenton et al. |
| 3,983,948 A | 10/1976 | Jeter |
| 3,985,133 A | 10/1976 | Jenkins et al. |
| 3,987,860 A | 10/1976 | Jabsen |
| 3,989,005 A | 11/1976 | Bowler, Jr. et al. |
| 3,991,749 A | 11/1976 | Zent |
| 3,992,948 A | 11/1976 | D'Antonio et al. |
| 3,993,149 A | 11/1976 | Harvey |
| 3,996,927 A | 12/1976 | Frank |
| 3,996,962 A | 12/1976 | Sutherland |
| 4,003,141 A | 1/1977 | Le Roy |
| 4,005,282 A | 1/1977 | Jennings |
| 4,005,593 A | 2/1977 | Goldberg |
| 4,006,735 A | 2/1977 | Hittman et al. |
| 4,009,375 A | 2/1977 | White et al. |
| 4,009,591 A | 3/1977 | Hester |
| 4,010,449 A | 3/1977 | Faggin et al. |
| 4,014,319 A | 3/1977 | Favre et al. |
| 4,014,321 A | 3/1977 | March |
| 4,016,764 A | 4/1977 | Rice |
| 4,017,329 A | 4/1977 | Larson |
| 4,018,134 A | 4/1977 | Linsinger et al. |
| 4,022,190 A | 5/1977 | Meyer |
| 4,024,864 A | 5/1977 | Davies et al. |
| 4,025,912 A | 5/1977 | Rice |
| 4,026,276 A | 5/1977 | Chubbuck |
| 4,027,661 A | 6/1977 | Lyon et al. |
| 4,031,899 A | 6/1977 | Renirie et al. |
| 4,036,775 A | 7/1977 | Trautvetter et al. |
| 4,039,069 A | 8/1977 | Kwan et al. |

| | | | | | |
|---|---|---|---|---|---|
| 4,041,954 A | 8/1977 | Ohara et al. | 4,170,280 A | 10/1979 | Schwarz |
| 4,042,504 A | 8/1977 | Drori et al. | 4,171,218 A | 10/1979 | Hoshino et al. |
| 4,045,345 A | 8/1977 | Drori et al. | 4,183,124 A | 1/1980 | Hoffman |
| 4,047,851 A | 9/1977 | Bender | 4,183,247 A | 1/1980 | Allen et al. |
| 4,048,494 A | 9/1977 | Liesting et al. | 4,185,641 A | 1/1980 | Minior et al. |
| 4,048,879 A | 9/1977 | Cox | 4,186,287 A | 1/1980 | Scott |
| 4,049,004 A | 9/1977 | Walters | 4,186,749 A | 2/1980 | Fryer |
| 4,051,338 A | 9/1977 | Harris, III | 4,186,751 A | 2/1980 | Fleischmann |
| 4,052,991 A | 10/1977 | Zacouto et al. | 4,190,057 A | 2/1980 | Hill et al. |
| 4,055,074 A | 10/1977 | Thimons et al. | 4,191,004 A | 3/1980 | Gmuer et al. |
| 4,055,175 A | 10/1977 | Clemens et al. | 4,191,187 A | 3/1980 | Wright et al. |
| 4,056,854 A | 11/1977 | Boretos et al. | 4,192,192 A | 3/1980 | Schnell |
| 4,058,007 A | 11/1977 | Exner et al. | 4,193,397 A | 3/1980 | Tucker et al. |
| 4,062,351 A | 12/1977 | Hastwell et al. | 4,204,547 A | 5/1980 | Allocca |
| 4,062,354 A | 12/1977 | Taylor et al. | 4,206,755 A | 6/1980 | Klein et al. |
| 4,062,360 A | 12/1977 | Bentley | 4,206,761 A | 6/1980 | Cosman |
| 4,063,439 A | 12/1977 | Besson et al. | 4,206,762 A | 6/1980 | Cosman |
| 4,064,882 A | 12/1977 | Johnson et al. | 4,207,903 A | 6/1980 | O'Neill |
| 4,070,239 A | 1/1978 | Bevilacqua | 4,212,074 A | 7/1980 | Kuno et al. |
| 4,072,047 A | 2/1978 | Reismuller et al. | 4,217,221 A | 8/1980 | Masso |
| 4,073,292 A | 2/1978 | Edelman | 4,217,588 A | 8/1980 | Freeny, Jr. |
| 4,075,099 A | 2/1978 | Pelton et al. | 4,220,189 A | 9/1980 | Marquez |
| 4,075,602 A | 2/1978 | Clothier | 4,221,219 A | 9/1980 | Tucker |
| 4,077,072 A | 3/1978 | Dezura et al. | 4,221,523 A | 9/1980 | Eberle |
| 4,077,394 A | 3/1978 | McCurdy | 4,223,837 A | 9/1980 | Gubbiotti et al. |
| 4,077,405 A | 3/1978 | Haerten et al. | 4,226,124 A | 10/1980 | Kersten et al. |
| 4,077,882 A | 3/1978 | Gangemi | 4,226,229 A | 10/1980 | Eckhart et al. |
| 4,078,620 A | 3/1978 | Westlake et al. | 4,227,533 A | 10/1980 | Godfrey |
| 4,080,653 A | 3/1978 | Barnes, Jr. et al. | 4,231,376 A | 11/1980 | Lyon et al. |
| 4,084,752 A | 4/1978 | Hagiwara et al. | 4,232,682 A | 11/1980 | Veth |
| 4,086,488 A | 4/1978 | Hill | 4,237,900 A | 12/1980 | Schulman et al. |
| 4,087,568 A | 5/1978 | Fay et al. | 4,241,247 A | 12/1980 | Byrne et al. |
| 4,088,417 A | 5/1978 | Kosmowski | 4,241,870 A | 12/1980 | Marcus |
| 4,089,329 A | 5/1978 | Couvillon, Jr. et al. | 4,245,593 A | 1/1981 | Stein |
| 4,090,802 A | 5/1978 | Bilz et al. | 4,246,877 A | 1/1981 | Kennedy |
| 4,092,719 A | 5/1978 | Salmon et al. | 4,247,850 A | 1/1981 | Marcus |
| 4,092,925 A | 6/1978 | Fromson | 4,248,238 A | 2/1981 | Joseph et al. |
| 4,096,866 A | 6/1978 | Fischell | 4,248,241 A | 2/1981 | Tacchi |
| 4,098,293 A | 7/1978 | Kramer et al. | 4,256,094 A | 3/1981 | Kapp et al. |
| 4,103,496 A | 8/1978 | Colamussi et al. | 4,256,118 A | 3/1981 | Nagel et al. |
| 4,106,370 A | 8/1978 | Kraus et al. | 4,262,343 A | 4/1981 | Claycomb |
| 4,107,689 A | 8/1978 | Jellinek | 4,262,632 A | 4/1981 | Hanton et al. |
| 4,107,995 A | 8/1978 | Ligman et al. | 4,265,241 A | 5/1981 | Portner et al. |
| 4,108,148 A | 8/1978 | Cannon, III | 4,265,252 A | 5/1981 | Chubbuck et al. |
| 4,108,575 A | 8/1978 | Schal et al. | 4,271,018 A | 6/1981 | Drori et al. |
| 4,109,148 A | 8/1978 | Jaulmes et al. | 4,273,070 A | 6/1981 | Hoefelmayr et al. |
| 4,109,518 A | 8/1978 | Dooley et al. | 4,274,444 A | 6/1981 | Ruyak |
| 4,109,644 A | 8/1978 | Kojima | 4,275,600 A | 6/1981 | Turner et al. |
| 4,111,056 A | 9/1978 | Mastromatteo | 4,275,913 A | 6/1981 | Marcus |
| 4,111,629 A | 9/1978 | Nussbaumer et al. | 4,278,540 A | 7/1981 | Drori et al. |
| 4,114,424 A | 9/1978 | Johnson | 4,280,036 A | 7/1981 | Fukatsu et al. |
| 4,114,606 A | 9/1978 | Seylar | 4,280,775 A | 7/1981 | Wood |
| 4,120,097 A | 10/1978 | Jeter | 4,281,666 A | 8/1981 | Cosman |
| 4,120,134 A | 10/1978 | Scholle | 4,281,667 A | 8/1981 | Cosman |
| 4,121,635 A | 10/1978 | Hansel | 4,284,073 A | 8/1981 | Krause et al. |
| 4,123,310 A | 10/1978 | Varon et al. | 4,285,770 A | 8/1981 | Chi et al. |
| 4,124,023 A | 11/1978 | Fleischmann et al. | 4,291,699 A | 9/1981 | Geddes et al. |
| 4,127,110 A | 11/1978 | Bullara | 4,295,963 A | 10/1981 | Drori et al. |
| 4,130,169 A | 12/1978 | Denison | 4,297,927 A | 11/1981 | Kuroda et al. |
| 4,131,596 A | 12/1978 | Allen | 4,303,075 A | 12/1981 | Heilman et al. |
| 4,133,355 A | 1/1979 | Mayer | 4,305,402 A | 12/1981 | Katims |
| 4,133,367 A | 1/1979 | Abell | 4,312,374 A | 1/1982 | Drori et al. |
| 4,140,131 A | 2/1979 | Dutcher et al. | 4,314,480 A | 2/1982 | Becker |
| 4,141,348 A | 2/1979 | Hittman | 4,316,693 A | 2/1982 | Baxter et al. |
| 4,141,349 A | 2/1979 | Ory et al. | 4,325,387 A | 4/1982 | Helfer |
| 4,143,661 A | 3/1979 | LaForge et al. | 4,327,804 A | 5/1982 | Reed |
| 4,146,029 A | 3/1979 | Ellinwood, Jr. | 4,328,654 A | 5/1982 | Van Ginkel et al. |
| 4,147,161 A | 4/1979 | Ikebe et al. | 4,332,254 A | 6/1982 | Lundquist |
| 4,148,096 A | 4/1979 | Haas et al. | 4,339,831 A | 7/1982 | Johnson |
| 4,149,423 A | 4/1979 | Frosch et al. | 4,342,218 A | 8/1982 | Fox |
| 4,151,823 A | 5/1979 | Grosse et al. | 4,342,308 A | 8/1982 | Trick |
| 4,153,085 A | 5/1979 | Adams | 4,346,604 A | 8/1982 | Snook et al. |
| 4,156,422 A | 5/1979 | Hildebrandt et al. | 4,347,851 A | 9/1982 | Jundanian |
| 4,160,448 A | 7/1979 | Jackson | 4,350,647 A | 9/1982 | de la Cruz |
| 4,160,971 A | 7/1979 | Jones et al. | 4,350,970 A | 9/1982 | von Tomkewitsch et al. |
| 4,166,469 A | 9/1979 | Littleford | 4,351,037 A | 9/1982 | Scherbatskoy |
| 4,167,304 A | 9/1979 | Gelbke | 4,351,116 A | 9/1982 | Scott, Jr. |
| 4,167,952 A | 9/1979 | Reinicke | 4,356,486 A | 10/1982 | Mount |
| 4,168,567 A | 9/1979 | Leguy et al. | 4,360,010 A | 11/1982 | Finney |

| | | | | | |
|---|---|---|---|---|---|
| 4,360,277 A | 11/1982 | Daniel et al. | 4,489,916 A | 12/1984 | Stevens |
| 4,361,153 A | 11/1982 | Slocum et al. | 4,492,632 A | 1/1985 | Mattson |
| 4,363,236 A | 12/1982 | Meyers | 4,494,411 A | 1/1985 | Koschke et al. |
| 4,364,276 A | 12/1982 | Shimazoe et al. | 4,494,950 A | 1/1985 | Fischell |
| 4,365,425 A | 12/1982 | Gotchel | 4,497,176 A | 2/1985 | Rubin et al. |
| 4,368,937 A | 1/1983 | Palombo et al. | 4,497,201 A | 2/1985 | Allen et al. |
| 4,369,013 A | 1/1983 | Abildgaard et al. | 4,499,394 A | 2/1985 | Koal |
| 4,373,527 A | 2/1983 | Fischell | 4,499,691 A | 2/1985 | Karazim et al. |
| 4,376,523 A | 3/1983 | Goyen et al. | 4,499,750 A | 2/1985 | Gerber et al. |
| 4,378,809 A | 4/1983 | Cosman | 4,503,678 A | 3/1985 | Wimbush et al. |
| 4,380,427 A | 4/1983 | Hehl | 4,511,974 A | 4/1985 | Nakane et al. |
| 4,385,636 A | 5/1983 | Cosman | 4,513,295 A | 4/1985 | Jones et al. |
| 4,386,422 A | 5/1983 | Mumby et al. | 4,515,004 A | 5/1985 | Jaenson |
| 4,387,907 A | 6/1983 | Hiestand et al. | 4,515,750 A | 5/1985 | Pardini et al. |
| 4,392,368 A | 7/1983 | Folkesson et al. | 4,516,866 A | 5/1985 | Yamauchi et al. |
| 4,393,899 A | 7/1983 | Tsuji et al. | 4,518,637 A | 5/1985 | Takeda et al. |
| 4,393,951 A | 7/1983 | Horst-Rudolf et al. | 4,519,401 A | 5/1985 | Ko et al. |
| 4,395,232 A | 7/1983 | Koch | 4,520,443 A | 5/1985 | Yuki et al. |
| 4,395,258 A | 7/1983 | Wang et al. | 4,522,213 A | 6/1985 | Wallroth et al. |
| 4,395,916 A | 8/1983 | Martin | 4,527,568 A | 7/1985 | Rickards et al. |
| 4,398,983 A | 8/1983 | Suzuki et al. | 4,529,401 A | 7/1985 | Leslie et al. |
| 4,399,705 A | 8/1983 | Weiger et al. | 4,531,526 A | 7/1985 | Genest |
| 4,399,707 A | 8/1983 | Wamstad | 4,531,936 A | 7/1985 | Gordon |
| 4,399,809 A | 8/1983 | Baro et al. | 4,536,000 A | 8/1985 | Rohm et al. |
| 4,399,821 A | 8/1983 | Bowers | 4,537,005 A | 8/1985 | Hoyland |
| 4,403,984 A | 9/1983 | Ash et al. | 4,537,129 A | 8/1985 | Heinemann et al. |
| 4,404,968 A | 9/1983 | Evans, Sr. | 4,538,616 A | 9/1985 | Rogoff |
| 4,404,974 A | 9/1983 | Titus | 4,540,404 A | 9/1985 | Wolvek |
| 4,405,318 A | 9/1983 | Whitney et al. | 4,542,461 A | 9/1985 | Eldridge et al. |
| 4,407,125 A | 10/1983 | Parsons et al. | 4,544,369 A | 10/1985 | Skakoon et al. |
| 4,407,271 A | 10/1983 | Schiff | 4,545,185 A | 10/1985 | Chikatani et al. |
| 4,407,296 A | 10/1983 | Anderson | 4,546,524 A | 10/1985 | Kreft |
| 4,407,326 A | 10/1983 | Wilhelm | 4,548,209 A | 10/1985 | Wielders et al. |
| 4,408,597 A | 10/1983 | Tenney, Jr. | 4,552,150 A | 11/1985 | Zacouto et al. |
| 4,408,615 A | 10/1983 | Grossman | 4,553,226 A | 11/1985 | Scherbatskoy |
| 4,415,071 A | 11/1983 | Butler et al. | 4,556,063 A | 12/1985 | Thompson et al. |
| 4,416,282 A | 11/1983 | Saulson et al. | 4,557,269 A | 12/1985 | Reynolds et al. |
| 4,418,899 A | 12/1983 | Zimmermann et al. | 4,557,332 A | 12/1985 | Denison et al. |
| 4,419,393 A | 12/1983 | Hanson et al. | 4,559,815 A | 12/1985 | Needham et al. |
| 4,421,505 A | 12/1983 | Schwartz | 4,560,979 A | 12/1985 | Rosskopf et al. |
| 4,424,720 A | 1/1984 | Bucchianeri | 4,561,442 A | 12/1985 | Vollmann et al. |
| 4,428,228 A | 1/1984 | Banzhaf et al. | 4,562,751 A | 1/1986 | Nason et al. |
| 4,428,365 A | 1/1984 | Hakky et al. | 4,563,175 A | 1/1986 | LaFond |
| 4,430,899 A | 2/1984 | Wessel et al. | 4,565,116 A | 1/1986 | Hehl et al. |
| 4,431,009 A | 2/1984 | Marino, Jr. et al. | 4,566,456 A | 1/1986 | Koning et al. |
| 4,431,365 A | 2/1984 | Sturtz, Jr. | 4,569,623 A | 2/1986 | Goldmann |
| 4,432,363 A | 2/1984 | Kakegawa et al. | 4,570,351 A | 2/1986 | Szanto et al. |
| 4,435,173 A | 3/1984 | Siposs et al. | 4,571,161 A | 2/1986 | Leblanc et al. |
| 4,439,186 A | 3/1984 | Kuhl et al. | 4,571,995 A | 2/1986 | Timme |
| 4,441,491 A | 4/1984 | Evans, Sr. | 4,573,835 A | 3/1986 | Eckardt et al. |
| 4,441,501 A | 4/1984 | Parent | 4,574,792 A | 3/1986 | Trick |
| 4,444,194 A | 4/1984 | Burcham | 4,576,181 A | 3/1986 | Wallace et al. |
| 4,444,498 A | 4/1984 | Heinemann | 4,576,183 A | 3/1986 | Plicchi et al. |
| 4,445,385 A | 5/1984 | Endo | 4,577,512 A | 3/1986 | Lowenheck et al. |
| 4,446,711 A | 5/1984 | Valente | 4,581,018 A | 4/1986 | Jassawalla et al. |
| 4,447,224 A | 5/1984 | DeCant, Jr. et al. | 4,581,915 A | 4/1986 | Haulsee et al. |
| 4,449,493 A | 5/1984 | Kopec et al. | 4,587,840 A | 5/1986 | Dobler et al. |
| 4,450,811 A | 5/1984 | Ichikawa et al. | 4,589,805 A | 5/1986 | Duffner et al. |
| 4,451,033 A | 5/1984 | Nestegard | 4,592,339 A | 6/1986 | Kuzmak et al. |
| 4,453,537 A | 6/1984 | Spitzer | 4,592,340 A | 6/1986 | Boyles |
| 4,453,578 A | 6/1984 | Wilder | 4,593,703 A | 6/1986 | Cosman |
| 4,460,835 A | 7/1984 | Masuoka et al. | 4,595,228 A | 6/1986 | Chu |
| 4,464,170 A | 8/1984 | Clemens et al. | 4,596,563 A | 6/1986 | Pande |
| 4,465,015 A | 8/1984 | Osta et al. | 4,599,943 A | 7/1986 | Kobler et al. |
| 4,465,474 A | 8/1984 | Mardorf et al. | 4,600,855 A | 7/1986 | Strachan et al. |
| 4,466,290 A | 8/1984 | Frick | 4,602,541 A | 7/1986 | Benzinger et al. |
| 4,468,172 A | 8/1984 | Dixon et al. | 4,604,089 A | 8/1986 | Santangelo et al. |
| 4,468,762 A | 8/1984 | Jurgens et al. | 4,605,354 A | 8/1986 | Daly |
| 4,469,365 A | 9/1984 | Marcus et al. | 4,606,419 A | 8/1986 | Perini |
| 4,471,182 A | 9/1984 | Wielgos et al. | 4,606,478 A | 8/1986 | Hack et al. |
| 4,471,786 A | 9/1984 | Inagaki et al. | 4,610,256 A | 9/1986 | Wallace |
| 4,473,067 A | 9/1984 | Schiff | 4,614,137 A | 9/1986 | Jones |
| 4,473,078 A | 9/1984 | Angel | 4,617,016 A | 10/1986 | Blomberg et al. |
| 4,476,721 A | 10/1984 | Hochreuther et al. | 4,618,861 A | 10/1986 | Gettens et al. |
| 4,478,213 A | 10/1984 | Redding | 4,620,807 A | 11/1986 | Polit |
| 4,478,538 A | 10/1984 | Kakino et al. | 4,621,331 A | 11/1986 | Iwata et al. |
| 4,483,196 A | 11/1984 | Kurtz et al. | 4,622,871 A | 11/1986 | Van Sickle et al. |
| 4,484,135 A | 11/1984 | Ishihara et al. | 4,626,462 A | 12/1986 | Kober et al. |
| 4,485,813 A | 12/1984 | Anderson et al. | 4,633,304 A | 12/1986 | Nagasaki et al. |

| | | | | | |
|---|---|---|---|---|---|
| 4,633,878 A | 1/1987 | Bombardieri et al. | 4,794,803 A | 1/1989 | Osterhout et al. |
| 4,635,182 A | 1/1987 | Hintz | 4,796,641 A | 1/1989 | Mills et al. |
| 4,637,736 A | 1/1987 | Andeen et al. | 4,798,211 A | 1/1989 | Goor et al. |
| 4,638,665 A | 1/1987 | Benson et al. | 4,798,227 A | 1/1989 | Goodwin |
| 4,644,246 A | 2/1987 | Knapen et al. | 4,799,491 A | 1/1989 | Eckerle |
| 4,646,553 A | 3/1987 | Tufte et al. | 4,799,625 A | 1/1989 | Weaver, Jr. et al. |
| 4,648,363 A | 3/1987 | Kronich | 4,802,488 A | 2/1989 | Eckerle |
| 4,648,406 A | 3/1987 | Miller | 4,803,987 A | 2/1989 | Calfee et al. |
| 4,658,358 A | 4/1987 | Leach et al. | 4,804,368 A | 2/1989 | Skakoon et al. |
| 4,658,760 A | 4/1987 | Zebuhr | 4,807,321 A | 2/1989 | Grasselli et al. |
| 4,660,568 A | 4/1987 | Cosman | 4,808,167 A | 2/1989 | Mann et al. |
| 4,665,511 A | 5/1987 | Rodney et al. | 4,812,823 A | 3/1989 | Dickerson |
| 4,665,896 A | 5/1987 | LaForge et al. | 4,819,656 A | 4/1989 | Spector |
| 4,669,484 A | 6/1987 | Masters | 4,820,265 A | 4/1989 | DeSatnick et al. |
| 4,672,974 A | 6/1987 | Lee | 4,820,953 A | 4/1989 | Saubolle et al. |
| 4,674,457 A | 6/1987 | Berger et al. | 4,821,167 A | 4/1989 | Wiebe |
| 4,674,546 A | 6/1987 | Fournier et al. | 4,821,723 A | 4/1989 | Baker, Jr. et al. |
| 4,678,408 A | 7/1987 | Nason et al. | 4,823,779 A | 4/1989 | Daly et al. |
| 4,681,559 A | 7/1987 | Hooven | 4,830,006 A | 5/1989 | Haluska et al. |
| 4,683,850 A | 8/1987 | Bauder et al. | 4,832,034 A | 5/1989 | Pizziconi et al. |
| 4,685,463 A | 8/1987 | Williams | 4,833,384 A | 5/1989 | Munro et al. |
| 4,685,469 A | 8/1987 | Keller et al. | 4,834,731 A | 5/1989 | Nowak et al. |
| 4,685,903 A | 8/1987 | Cable et al. | 4,838,857 A | 6/1989 | Strowe et al. |
| 4,686,987 A | 8/1987 | Salo et al. | 4,840,068 A | 6/1989 | Mayhew, Jr. |
| 4,687,530 A | 8/1987 | Berscheid et al. | 4,840,350 A | 6/1989 | Cook et al. |
| 4,689,979 A | 9/1987 | Otsuka et al. | 4,844,002 A | 7/1989 | Yasui et al. |
| 4,691,694 A | 9/1987 | Boyd et al. | 4,846,153 A | 7/1989 | Berci |
| 4,691,710 A | 9/1987 | Dickens et al. | 4,846,191 A | 7/1989 | Brockway et al. |
| 4,693,253 A | 9/1987 | Adams | 4,846,664 A | 7/1989 | Hehl et al. |
| 4,695,237 A | 9/1987 | Inaba et al. | 4,854,328 A | 8/1989 | Pollack |
| 4,696,189 A | 9/1987 | Hochreuther et al. | 4,863,470 A | 9/1989 | Carter |
| 4,697,574 A | 10/1987 | Karcher et al. | 4,865,587 A | 9/1989 | Walling |
| 4,698,038 A | 10/1987 | Key et al. | 4,867,160 A | 9/1989 | Schaldach et al. |
| 4,700,497 A | 10/1987 | Sato et al. | 4,867,498 A | 9/1989 | Delphia et al. |
| 4,700,610 A | 10/1987 | Bauer et al. | 4,867,618 A | 9/1989 | Brohammer |
| 4,701,143 A | 10/1987 | Key et al. | 4,869,252 A | 9/1989 | Gilli |
| 4,703,756 A | 11/1987 | Gough et al. | 4,870,258 A | 9/1989 | Mochizuki et al. |
| 4,705,507 A | 11/1987 | Boyles | 4,871,351 A | 10/1989 | Feingold et al. |
| 4,706,948 A | 11/1987 | Kroecher et al. | 4,872,483 A | 10/1989 | Shah |
| 4,712,562 A | 12/1987 | Ohayon et al. | 4,872,869 A | 10/1989 | Johns |
| 4,718,425 A | 1/1988 | Tanaka et al. | 4,873,677 A | 10/1989 | Sakamoto et al. |
| 4,722,348 A | 2/1988 | Ligtenberg et al. | 4,875,483 A | 10/1989 | Vollmann et al. |
| 4,724,806 A | 2/1988 | Hartwig et al. | 4,880,004 A | 11/1989 | Baker, Jr. et al. |
| 4,724,830 A | 2/1988 | Fischell | 4,882,678 A | 11/1989 | Hollis et al. |
| 4,725,826 A | 2/1988 | Hunter | 4,886,392 A | 12/1989 | Iio et al. |
| 4,728,479 A | 3/1988 | Merkovsky | 4,895,151 A | 1/1990 | Grevis et al. |
| 4,729,517 A | 3/1988 | Krokor et al. | 4,896,594 A | 1/1990 | Baur et al. |
| 4,730,188 A | 3/1988 | Milheiser | 4,898,158 A | 2/1990 | Daly et al. |
| 4,730,420 A | 3/1988 | Stratmann et al. | 4,898,578 A | 2/1990 | Rubalcaba, Jr. |
| 4,730,619 A | 3/1988 | Koning et al. | 4,899,751 A | 2/1990 | Cohen |
| 4,731,058 A | 3/1988 | Doan | 4,899,752 A | 2/1990 | Cohen |
| 4,735,205 A | 4/1988 | Chachques et al. | 4,902,277 A | 2/1990 | Mathies et al. |
| 4,738,267 A | 4/1988 | Lazorthes et al. | 4,903,701 A | 2/1990 | Moore et al. |
| 4,738,268 A | 4/1988 | Kipnis | 4,909,678 A | 3/1990 | Kakimoto et al. |
| 4,741,345 A | 5/1988 | Matthews et al. | 4,913,147 A | 4/1990 | Fahlstrom et al. |
| 4,741,732 A | 5/1988 | Crankshaw et al. | 4,919,143 A | 4/1990 | Ayers |
| 4,743,129 A | 5/1988 | Keryhuel et al. | 4,924,872 A | 5/1990 | Frank |
| 4,745,541 A | 5/1988 | Vaniglia et al. | 4,926,903 A | 5/1990 | Kawai et al. |
| 4,746,830 A | 5/1988 | Holland | 4,932,406 A | 6/1990 | Berkovits |
| 4,750,495 A | 6/1988 | Moore et al. | 4,934,369 A | 6/1990 | Maxwell |
| 4,752,115 A | 6/1988 | Murray, Jr. et al. | 4,936,304 A | 6/1990 | Kresh et al. |
| 4,752,658 A | 6/1988 | Mack | 4,940,037 A | 7/1990 | Eckert et al. |
| 4,757,463 A | 7/1988 | Ballou et al. | 4,941,718 A | 7/1990 | Alexander, III et al. |
| 4,759,386 A | 7/1988 | Grouw, III | 4,942,004 A | 7/1990 | Catanzaro |
| 4,763,649 A | 8/1988 | Merrick | 4,944,050 A | 7/1990 | Shames et al. |
| 4,765,001 A | 8/1988 | Smith | 4,944,298 A | 7/1990 | Sholder |
| 4,767,406 A | 8/1988 | Wadham et al. | 4,944,307 A | 7/1990 | Hon et al. |
| 4,769,001 A | 9/1988 | Prince | 4,945,761 A | 8/1990 | Lessi et al. |
| 4,772,896 A | 9/1988 | Nakatsu et al. | 4,949,724 A | 8/1990 | Mahutte et al. |
| 4,773,401 A | 9/1988 | Citak et al. | 4,952,205 A | 8/1990 | Mauerer et al. |
| 4,774,950 A | 10/1988 | Cohen | 4,952,928 A | 8/1990 | Carroll et al. |
| 4,774,955 A | 10/1988 | Jones | 4,953,563 A | 9/1990 | Kaiser et al. |
| 4,777,953 A | 10/1988 | Ash et al. | 4,954,677 A | 9/1990 | Alberter et al. |
| 4,779,626 A | 10/1988 | Peel et al. | 4,958,630 A | 9/1990 | Rosenbluth et al. |
| 4,781,192 A | 11/1988 | Demer | 4,958,645 A | 9/1990 | Cadell et al. |
| 4,782,826 A | 11/1988 | Fogarty | 4,960,424 A | 10/1990 | Grooters |
| 4,783,106 A | 11/1988 | Nutter | 4,960,966 A | 10/1990 | Evans et al. |
| 4,788,847 A | 12/1988 | Sterghos | 4,967,585 A | 11/1990 | Grimaldo |
| 4,791,318 A | 12/1988 | Lewis et al. | 4,967,761 A | 11/1990 | Nathanielsz |

| | | |
|---|---|---|
| 4,970,823 A | 11/1990 | Chen et al. |
| 4,971,251 A | 11/1990 | Dobrick et al. |
| 4,977,896 A | 12/1990 | Robinson et al. |
| 4,978,335 A | 12/1990 | Arthur, III |
| 4,978,338 A | 12/1990 | Melsky et al. |
| 4,979,730 A | 12/1990 | Holbrook et al. |
| 4,980,671 A | 12/1990 | McCurdy |
| 4,981,141 A | 1/1991 | Segalowitz |
| 4,981,173 A | 1/1991 | Perkins et al. |
| 4,981,426 A | 1/1991 | Aoki et al. |
| 4,987,897 A | 1/1991 | Funke et al. |
| 4,988,337 A | 1/1991 | Ito et al. |
| 4,992,794 A | 2/1991 | Brouwers et al. |
| 4,997,556 A | 3/1991 | Yano et al. |
| 5,001,528 A | 3/1991 | Bahraman |
| 5,003,807 A | 4/1991 | Terrell et al. |
| 5,003,975 A | 4/1991 | Hafelfinger et al. |
| 5,003,976 A | 4/1991 | Alt et al. |
| 5,004,472 A | 4/1991 | Wallace |
| 5,004,873 A | 4/1991 | Schnut |
| 5,005,574 A | 4/1991 | Fearnot et al. |
| 5,005,586 A | 4/1991 | Lahr |
| 5,006,844 A | 4/1991 | Ohta et al. |
| 5,007,401 A | 4/1991 | Grohn et al. |
| 5,007,430 A | 4/1991 | Dardik |
| 5,007,919 A | 4/1991 | Silva et al. |
| 5,009,662 A | 4/1991 | Wallace et al. |
| 5,010,893 A | 4/1991 | Sholder |
| 5,012,286 A | 4/1991 | Kawano et al. |
| 5,012,810 A | 5/1991 | Strand et al. |
| 5,013,292 A | 5/1991 | Lemay et al. |
| 5,014,040 A | 5/1991 | Weaver et al. |
| 5,019,032 A | 5/1991 | Robertson |
| 5,019,041 A | 5/1991 | Robinson et al. |
| 5,020,845 A | 6/1991 | Falcoff et al. |
| 5,021,046 A | 6/1991 | Wallace |
| 5,022,395 A | 6/1991 | Russie |
| 5,024,965 A | 6/1991 | Chang et al. |
| 5,026,180 A | 6/1991 | Tajima et al. |
| 5,026,360 A | 6/1991 | Johnsen et al. |
| 5,028,918 A | 7/1991 | Giles et al. |
| 5,032,822 A | 7/1991 | Sweet |
| 5,036,869 A | 8/1991 | Inahara et al. |
| 5,038,800 A | 8/1991 | Oba et al. |
| 5,041,086 A | 8/1991 | Koenig et al. |
| 5,041,826 A | 8/1991 | Milheiser |
| 5,042,503 A | 8/1991 | Torok et al. |
| 5,044,770 A | 9/1991 | Haghkar |
| 5,046,661 A | 9/1991 | Kimura et al. |
| 5,048,060 A | 9/1991 | Arai et al. |
| 5,050,922 A | 9/1991 | Falcoff |
| 5,052,910 A | 10/1991 | Hehl et al. |
| 5,053,008 A | 10/1991 | Bajaj |
| 5,057,078 A | 10/1991 | Foote et al. |
| 5,058,583 A | 10/1991 | Geddes et al. |
| 5,061,239 A | 10/1991 | Shiels |
| 5,062,052 A | 10/1991 | Sparer et al. |
| 5,062,053 A | 10/1991 | Shirai et al. |
| 5,062,559 A | 11/1991 | Falcoff |
| 5,064,974 A | 11/1991 | Vigneau et al. |
| 5,067,960 A | 11/1991 | Grandjean et al. |
| 5,068,779 A | 11/1991 | Sullivan et al. |
| 5,069,680 A | 12/1991 | Grandjean et al. |
| 5,077,102 A | 12/1991 | Chong |
| 5,077,870 A | 1/1992 | Melbye et al. |
| 5,078,139 A | 1/1992 | Strand et al. |
| 5,082,006 A | 1/1992 | Jonasson et al. |
| 5,083,563 A | 1/1992 | Collins et al. |
| 5,084,699 A | 1/1992 | DeMichele |
| 5,085,224 A | 2/1992 | Galen et al. |
| 5,085,258 A | 2/1992 | Fink, Jr. et al. |
| 5,089,673 A | 2/1992 | Strzodka et al. |
| 5,089,979 A | 2/1992 | McEachern et al. |
| 5,095,309 A | 3/1992 | Troyk et al. |
| 5,096,271 A | 3/1992 | Portman |
| 5,097,831 A | 3/1992 | Lekholm |
| 5,098,384 A | 3/1992 | Abrams |
| 5,103,832 A | 4/1992 | Jackson |
| 5,105,810 A | 4/1992 | Collins et al. |
| 5,107,850 A | 4/1992 | Olive |
| 5,112,344 A | 5/1992 | Petros et al. |
| 5,113,859 A | 5/1992 | Funke et al. |
| 5,113,869 A | 5/1992 | Nappholz et al. |
| 5,115,676 A | 5/1992 | Lee |
| 5,117,825 A | 6/1992 | Grevious |
| 5,121,777 A | 6/1992 | Leininger et al. |
| 5,127,451 A | 7/1992 | Fink, Jr. et al. |
| 5,129,394 A | 7/1992 | Mehra |
| 5,129,806 A | 7/1992 | Hehl et al. |
| 5,131,145 A | 7/1992 | Badoureaux et al. |
| 5,131,388 A | 7/1992 | Pless et al. |
| 5,133,358 A | 7/1992 | Gustafson et al. |
| 5,135,488 A | 8/1992 | Foote et al. |
| 5,139,484 A | 8/1992 | Hazon et al. |
| 5,144,949 A | 9/1992 | Olson |
| 5,148,580 A | 9/1992 | Dyckow et al. |
| 5,148,695 A | 9/1992 | Ellis |
| 5,152,770 A | 10/1992 | Bengmark et al. |
| 5,152,776 A | 10/1992 | Pinchuk |
| 5,154,170 A | 10/1992 | Bennett et al. |
| 5,154,171 A | 10/1992 | Chirife et al. |
| 5,154,693 A | 10/1992 | East et al. |
| 5,156,972 A | 10/1992 | Issachar et al. |
| 5,158,078 A | 10/1992 | Bennett et al. |
| 5,163,429 A | 11/1992 | Cohen |
| 5,167,615 A | 12/1992 | East et al. |
| 5,168,757 A | 12/1992 | Rabenau et al. |
| 5,168,982 A | 12/1992 | Hakanen et al. |
| 5,171,299 A | 12/1992 | Heitzmann et al. |
| 5,173,873 A | 12/1992 | Wu et al. |
| 5,174,286 A | 12/1992 | Chirife et al. |
| 5,174,291 A | 12/1992 | Schoonen et al. |
| 5,176,502 A | 1/1993 | Sanderson et al. |
| 5,178,197 A | 1/1993 | Healy |
| 5,181,423 A | 1/1993 | Philipps et al. |
| 5,181,517 A | 1/1993 | Hickey |
| 5,184,132 A | 2/1993 | Baird |
| 5,184,614 A | 2/1993 | Collins et al. |
| 5,184,619 A | 2/1993 | Austin |
| 5,185,535 A | 2/1993 | Farb et al. |
| 5,186,224 A | 2/1993 | Schirmacher et al. |
| 5,188,106 A | 2/1993 | Nappholz et al. |
| 5,188,604 A | 2/1993 | Orth |
| 5,192,314 A | 3/1993 | Daskalakis |
| 5,195,362 A | 3/1993 | Eason |
| 5,197,322 A | 3/1993 | Indravudh |
| 5,199,427 A | 4/1993 | Strickland |
| 5,199,428 A | 4/1993 | Obel et al. |
| 5,201,753 A | 4/1993 | Lampropoulos et al. |
| 5,204,670 A | 4/1993 | Stinton |
| 5,207,429 A | 5/1993 | Walmsley et al. |
| 5,209,223 A | 5/1993 | McGorry et al. |
| 5,209,732 A | 5/1993 | Lampropoulos et al. |
| 5,211,129 A | 5/1993 | Taylor et al. |
| 5,211,161 A | 5/1993 | Stef et al. |
| 5,212,476 A | 5/1993 | Maloney |
| 5,213,331 A | 5/1993 | Avanzini |
| 5,215,523 A | 6/1993 | Williams et al. |
| 5,218,343 A | 6/1993 | Stobbe et al. |
| 5,218,957 A | 6/1993 | Strickland |
| 5,226,429 A | 7/1993 | Kuzmak |
| 5,226,604 A | 7/1993 | Seiffert et al. |
| 5,230,694 A | 7/1993 | Rosenblum |
| 5,233,985 A | 8/1993 | Hudrlik |
| 5,235,326 A | 8/1993 | Beigel et al. |
| 5,244,269 A | 9/1993 | Harriehausen et al. |
| 5,244,461 A | 9/1993 | Derlien et al. |
| 5,246,008 A | 9/1993 | Mueller et al. |
| 5,249,858 A | 10/1993 | Nusser |
| 5,250,020 A | 10/1993 | Bley |
| 5,254,096 A | 10/1993 | Rondelet et al. |
| 5,256,157 A | 10/1993 | Samiotes et al. |
| 5,263,244 A | 11/1993 | Centa et al. |
| 5,263,981 A | 11/1993 | Polyak et al. |
| 5,267,940 A | 12/1993 | Moulder |
| 5,267,942 A | 12/1993 | Saperston |
| 5,269,891 A | 12/1993 | Colin et al. |
| 5,271,395 A | 12/1993 | Wahlstrand et al. |

| | | | | | | |
|---|---|---|---|---|---|---|
| 5,274,859 | A | 1/1994 | Redman et al. | 5,487,760 A | 1/1996 | Villafana |
| 5,280,789 | A | 1/1994 | Potts | 5,493,738 A | 2/1996 | Sanderson et al. |
| 5,282,839 | A | 2/1994 | Roline et al. | 5,494,036 A | 2/1996 | Uber, III et al. |
| 5,282,840 | A | 2/1994 | Hudrlik | 5,494,193 A | 2/1996 | Kirschner et al. |
| 5,291,894 | A | 3/1994 | Nagy et al. | 5,504,474 A | 4/1996 | Libman et al. |
| 5,292,219 | A | 3/1994 | Merin et al. | 5,505,916 A | 4/1996 | Berry, Jr. |
| 5,295,967 | A | 3/1994 | Rondelet et al. | 5,507,412 A | 4/1996 | Ebert et al. |
| 5,298,022 | A | 3/1994 | Bernardi et al. | 5,507,737 A | 4/1996 | Palmskog et al. |
| 5,298,884 | A | 3/1994 | Gilmore et al. | 5,507,785 A | 4/1996 | Deno |
| 5,300,093 | A | 4/1994 | Koestner et al. | 5,509,888 A | 4/1996 | Miller |
| 5,300,120 | A | 4/1994 | Knapp et al. | 5,509,891 A | 4/1996 | DeRidder |
| 5,304,112 | A | 4/1994 | Mrklas et al. | 5,513,945 A | 5/1996 | Hartmann et al. |
| 5,305,923 | A | 4/1994 | Kirschner et al. | 5,514,103 A | 5/1996 | Srisathapat et al. |
| 5,312,443 | A | 5/1994 | Adams et al. | 5,518,504 A | 5/1996 | Polyak |
| 5,312,452 | A | 5/1994 | Salo | 5,520,606 A | 5/1996 | Schoolman et al. |
| 5,312,453 | A | 5/1994 | Shelton et al. | 5,523,740 A | 6/1996 | Burgmann et al. |
| 5,313,953 | A | 5/1994 | Yomtov et al. | 5,534,018 A | 7/1996 | Wahlstrand et al. |
| 5,314,451 | A | 5/1994 | Mulier | 5,535,752 A | 7/1996 | Halperin et al. |
| 5,314,457 | A | 5/1994 | Jeutter et al. | 5,538,005 A | 7/1996 | Harrison et al. |
| 5,324,315 | A | 6/1994 | Grevious | 5,541,857 A | 7/1996 | Walter et al. |
| 5,325,834 | A | 7/1994 | Ballheimer et al. | 5,545,140 A | 8/1996 | Conero et al. |
| 5,326,249 | A | 7/1994 | Weissfloch et al. | 5,545,151 A | 8/1996 | O'Connor et al. |
| 5,328,460 | A | 7/1994 | Lord et al. | 5,545,186 A | 8/1996 | Olson et al. |
| 5,330,511 | A | 7/1994 | Boute et al. | 5,545,214 A | 8/1996 | Stevens |
| 5,337,750 | A | 8/1994 | Walloch | 5,547,470 A | 8/1996 | Johnson et al. |
| 5,341,430 | A | 8/1994 | Aulia et al. | 5,551,427 A | 9/1996 | Altman |
| 5,342,401 | A | 8/1994 | Spano et al. | 5,551,439 A | 9/1996 | Hickey |
| 5,342,406 | A | 8/1994 | Thompson | 5,554,185 A | 9/1996 | Block et al. |
| 5,344,388 | A | 9/1994 | Maxwell et al. | 5,558,644 A | 9/1996 | Boyd et al. |
| 5,347,476 | A | 9/1994 | McBean, Sr. | 5,564,434 A | 10/1996 | Halperin et al. |
| 5,348,210 | A | 9/1994 | Linzell et al. | 5,575,770 A | 11/1996 | Melsky et al. |
| 5,348,536 | A | 9/1994 | Young et al. | 5,584,803 A | 12/1996 | Stevens et al. |
| 5,350,413 | A | 9/1994 | Miller et al. | 5,586,629 A | 12/1996 | Shoberg et al. |
| 5,352,180 | A | 10/1994 | Candelon et al. | 5,593,430 A | 1/1997 | Renger |
| 5,353,622 | A | 10/1994 | Theener | 5,594,665 A | 1/1997 | Walter et al. |
| 5,353,800 | A | 10/1994 | Pohndorf et al. | 5,596,986 A | 1/1997 | Goldfarb |
| 5,354,200 | A | 10/1994 | Klein et al. | 5,597,284 A | 1/1997 | Weltlich et al. |
| 5,354,316 | A | 10/1994 | Keimel | 5,610,083 A | 3/1997 | Chan et al. |
| 5,354,319 | A | 10/1994 | Wyborny et al. | 5,611,768 A | 3/1997 | Tutrone, Jr. |
| 5,360,407 | A | 11/1994 | Leonard et al. | 5,612,497 A | 3/1997 | Walter et al. |
| 5,365,462 | A | 11/1994 | McBean, Sr. | 5,615,671 A | 4/1997 | Schoonen et al. |
| 5,365,619 | A | 11/1994 | Solomon | 5,619,991 A | 4/1997 | Sloane |
| 5,365,985 | A | 11/1994 | Todd et al. | 5,625,946 A | 5/1997 | Wildeson et al. |
| 5,368,040 | A | 11/1994 | Carney | 5,626,623 A | 5/1997 | Kieval et al. |
| 5,370,665 | A | 12/1994 | Hudrlik | 5,626,630 A | 5/1997 | Markowitz et al. |
| 5,373,852 | A | 12/1994 | Harrison et al. | 5,630,836 A | 5/1997 | Prem et al. |
| 5,375,073 | A | 12/1994 | McBean | 5,634,255 A | 6/1997 | Bishop et al. |
| 5,377,128 | A | 12/1994 | McBean | 5,637,083 A | 6/1997 | Bertrand et al. |
| 5,378,231 | A | 1/1995 | Johnson et al. | 5,643,207 A | 7/1997 | Rise |
| 5,382,232 | A | 1/1995 | Hague et al. | 5,645,116 A | 7/1997 | McDonald |
| 5,383,915 | A | 1/1995 | Adams | 5,650,766 A | 7/1997 | Burgmann et al. |
| 5,388,578 | A | 2/1995 | Yomtov et al. | 5,673,585 A | 10/1997 | Bishop et al. |
| 5,388,586 | A | 2/1995 | Lee et al. | 5,676,690 A | 10/1997 | Noren et al. |
| 5,388,831 | A | 2/1995 | Quadri et al. | 5,681,285 A | 10/1997 | Ford et al. |
| 5,394,909 | A | 3/1995 | Mitchell et al. | 5,686,831 A | 11/1997 | Vandervalk et al. |
| 5,402,944 | A | 4/1995 | Pape et al. | 5,687,734 A | 11/1997 | Dempsey et al. |
| 5,406,957 | A | 4/1995 | Tansey | 5,693,076 A | 12/1997 | Kaemmerer |
| 5,409,009 | A | 4/1995 | Olson | 5,702,368 A | 12/1997 | Stevens et al. |
| 5,411,031 | A | 5/1995 | Yomtov | 5,702,427 A | 12/1997 | Ecker et al. |
| 5,411,551 | A | 5/1995 | Winston et al. | 5,702,431 A | 12/1997 | Wang et al. |
| 5,411,552 | A | 5/1995 | Andersen et al. | 5,704,352 A | 1/1998 | Tremblay et al. |
| 5,416,372 | A | 5/1995 | Ljungstroem et al. | 5,715,786 A | 2/1998 | Seiberth et al. |
| 5,417,226 | A | 5/1995 | Juma | 5,715,837 A | 2/1998 | Chen |
| 5,417,717 | A | 5/1995 | Salo et al. | 5,720,436 A | 2/1998 | Buschor et al. |
| 5,425,362 | A | 6/1995 | Siker et al. | 5,730,101 A | 3/1998 | Aupperle et al. |
| 5,431,171 | A | 7/1995 | Harrison et al. | 5,732,710 A | 3/1998 | Rabinovich et al. |
| 5,431,694 | A | 7/1995 | Snaper et al. | 5,733,313 A | 3/1998 | Barreras, Sr. et al. |
| 5,433,694 | A | 7/1995 | Lim et al. | 5,738,652 A | 4/1998 | Boyd et al. |
| 5,437,605 | A | 8/1995 | Helmy et al. | 5,742,233 A | 4/1998 | Hoffman et al. |
| 5,443,215 | A | 8/1995 | Fackler | 5,743,267 A | 4/1998 | Nikolic et al. |
| 5,447,519 | A | 9/1995 | Peterson | 5,749,369 A | 5/1998 | Rabinovich et al. |
| 5,449,368 | A | 9/1995 | Kuzmak | 5,749,909 A | 5/1998 | Schroeppel et al. |
| 5,456,690 | A | 10/1995 | Duong-Van | 5,755,687 A | 5/1998 | Donlon |
| 5,461,390 | A | 10/1995 | Hoshen | 5,755,748 A | 5/1998 | Borza et al. |
| 5,464,435 | A | 11/1995 | Neumann | 5,765,568 A | 6/1998 | Sweezer, Jr. et al. |
| 5,467,627 | A | 11/1995 | Smith et al. | 5,769,812 A | 6/1998 | Stevens et al. |
| 5,474,226 | A | 12/1995 | Joseph | 5,771,903 A | 6/1998 | Jakobsson |
| 5,479,818 | A | 1/1996 | Walter et al. | 5,782,774 A | 7/1998 | Shmulewitz |
| 5,482,049 | A | 1/1996 | Addiss et al. | 5,787,520 A | 8/1998 | Dunbar |

| | | |
|---|---|---|
| 5,791,344 A | 8/1998 | Schulman et al. |
| 5,792,094 A | 8/1998 | Stevens et al. |
| 5,792,179 A | 8/1998 | Sideris |
| 5,795,325 A | 8/1998 | Valley et al. |
| 5,796,827 A | 8/1998 | Coppersmith et al. |
| 5,800,375 A | 9/1998 | Sweezer et al. |
| 5,807,265 A | 9/1998 | Itoigawa et al. |
| 5,807,336 A | 9/1998 | Russo et al. |
| 5,810,015 A | 9/1998 | Flaherty |
| 5,810,757 A | 9/1998 | Sweezer, Jr. et al. |
| 5,814,016 A | 9/1998 | Valley et al. |
| 5,817,093 A | 10/1998 | Williamson, IV et al. |
| 5,833,603 A | 11/1998 | Kovacs et al. |
| 5,836,300 A | 11/1998 | Mault |
| 5,836,886 A | 11/1998 | Itoigawa et al. |
| 5,840,081 A | 11/1998 | Andersen et al. |
| 5,849,225 A | 12/1998 | Ebina et al. |
| 5,855,597 A | 1/1999 | Jayaraman et al. |
| 5,855,601 A | 1/1999 | Bessler et al. |
| 5,860,938 A | 1/1999 | Lafontaine et al. |
| 5,861,018 A | 1/1999 | Feierbach |
| 5,863,366 A | 1/1999 | Snow |
| 5,868,702 A | 2/1999 | Stevens et al. |
| 5,873,837 A | 2/1999 | Lieber et al. |
| 5,875,953 A | 3/1999 | Shioya et al. |
| 5,879,499 A | 3/1999 | Corvi |
| 5,881,919 A | 3/1999 | Womac et al. |
| 5,885,238 A | 3/1999 | Stevens et al. |
| 5,887,475 A | 3/1999 | Muldner |
| 5,899,927 A | 5/1999 | Ecker et al. |
| 5,916,179 A | 6/1999 | Sharrock |
| 5,916,237 A | 6/1999 | Schu |
| 5,935,078 A | 8/1999 | Feierbach |
| 5,938,669 A | 8/1999 | Klaiber et al. |
| 5,951,487 A | 9/1999 | Brehmeier-Flick et al. |
| 5,957,861 A | 9/1999 | Combs et al. |
| 5,967,986 A | 10/1999 | Cimochowski et al. |
| 5,971,934 A | 10/1999 | Scherer et al. |
| 5,974,873 A | 11/1999 | Nelson et al. |
| 5,978,985 A | 11/1999 | Thurman |
| 5,995,874 A | 11/1999 | Borza et al. |
| 6,015,386 A | 1/2000 | Kensey et al. |
| 6,015,387 A | 1/2000 | Schwartz et al. |
| 6,019,729 A | 2/2000 | Itoigawa et al. |
| 6,024,704 A | 2/2000 | Meador et al. |
| 6,030,413 A | 2/2000 | Lazarus |
| 6,035,461 A | 3/2000 | Nguyen |
| 6,053,873 A | 4/2000 | Govari et al. |
| 6,056,723 A | 5/2000 | Donlon |
| 6,058,330 A | 5/2000 | Borza et al. |
| 6,059,757 A | 5/2000 | Macoviak et al. |
| 6,067,474 A | 5/2000 | Schulman et al. |
| 6,067,991 A | 5/2000 | Forsell et al. |
| 6,076,016 A | 6/2000 | Feierbach |
| 6,083,174 A | 7/2000 | Brehmeier-Flick et al. |
| 6,090,096 A | 7/2000 | St. Goar et al. |
| 6,102,678 A | 8/2000 | Peclat et al. |
| 6,102,856 A | 8/2000 | Groff et al. |
| 6,102,922 A | 8/2000 | Jakobsson et al. |
| 6,106,477 A | 8/2000 | Miesel et al. |
| 6,106,551 A | 8/2000 | Crossett et al. |
| 6,110,145 A | 8/2000 | Macoviak |
| 6,113,553 A | 9/2000 | Chubbuck |
| 6,131,664 A | 10/2000 | Sonnier |
| 6,135,945 A | 10/2000 | Sultan |
| 6,159,156 A | 12/2000 | Van Bockel et al. |
| 6,162,180 A | 12/2000 | Miesel et al. |
| 6,162,245 A | 12/2000 | Jayaraman et al. |
| 6,168,614 B1 | 1/2001 | Andersen et al. |
| 6,234,745 B1 | 5/2001 | Pugh et al. |
| 6,240,316 B1 | 5/2001 | Richmond et al. |
| 6,240,318 B1 | 5/2001 | Phillips |
| 6,245,102 B1 | 6/2001 | Jayaraman |
| 6,248,080 B1 | 6/2001 | Miesel et al. |
| 6,251,093 B1 | 6/2001 | Valley et al. |
| 6,269,819 B1 | 8/2001 | Oz et al. |
| 6,277,078 B1 | 8/2001 | Porat et al. |
| 6,292,697 B1 | 9/2001 | Roberts |
| 6,309,350 B1 | 10/2001 | VanTassel et al. |
| 6,315,769 B1 | 11/2001 | Peer et al. |
| 6,319,208 B1 | 11/2001 | Abita et al. |
| 6,328,699 B1 | 12/2001 | Eigler et al. |
| 6,338,735 B1 | 1/2002 | Stevens |
| 6,357,438 B1 | 3/2002 | Hansen |
| 6,360,122 B1 | 3/2002 | Fischell et al. |
| 6,360,822 B1 | 3/2002 | Robertson et al. |
| 6,366,817 B1 | 4/2002 | Kung |
| 6,379,308 B1 | 4/2002 | Brockway et al. |
| 6,379,380 B1 | 4/2002 | Satz |
| 6,398,752 B1 | 6/2002 | Sweezer, Jr. et al. |
| 6,409,674 B1 | 6/2002 | Brockway et al. |
| 6,423,031 B1 | 7/2002 | Donlon |
| 6,430,444 B1 | 8/2002 | Borza et al. |
| 6,431,175 B1 | 8/2002 | Penner et al. |
| 6,432,040 B1 | 8/2002 | Meah |
| 6,443,887 B1 | 9/2002 | Derus et al. |
| 6,443,893 B1 | 9/2002 | Schnakenberg et al. |
| 6,450,173 B1 | 9/2002 | Forsell et al. |
| 6,450,946 B1 | 9/2002 | Forsell et al. |
| 6,453,907 B1 | 9/2002 | Forsell et al. |
| 6,454,698 B1 | 9/2002 | Forsell et al. |
| 6,454,699 B1 | 9/2002 | Forsell et al. |
| 6,454,700 B1 | 9/2002 | Forsell et al. |
| 6,454,701 B1 | 9/2002 | Forsell et al. |
| 6,461,292 B1 | 10/2002 | Forsell et al. |
| 6,461,293 B1 | 10/2002 | Forsell et al. |
| 6,463,329 B1 | 10/2002 | Goedeke |
| 6,463,935 B1 | 10/2002 | Forsell et al. |
| 6,464,628 B1 | 10/2002 | Forsell et al. |
| 6,470,212 B1 | 10/2002 | Weijand et al. |
| 6,470,892 B1 | 10/2002 | Forsell et al. |
| 6,471,635 B1 | 10/2002 | Forsell et al. |
| 6,475,136 B1 | 11/2002 | Forsell et al. |
| 6,475,170 B1 | 11/2002 | Doron et al. |
| 6,482,145 B1 | 11/2002 | Forsell et al. |
| 6,482,171 B1 | 11/2002 | Corvi et al. |
| 6,482,177 B1 | 11/2002 | Leinders et al. |
| 6,486,588 B2 | 11/2002 | Doron et al. |
| 6,503,189 B1 | 1/2003 | Forsell et al. |
| 6,504,286 B1 | 1/2003 | Porat et al. |
| 6,531,739 B2 | 3/2003 | Cable et al. |
| 6,533,719 B2 | 3/2003 | Kuyava et al. |
| 6,533,733 B1 | 3/2003 | Ericson et al. |
| 6,542,350 B1 | 4/2003 | Rogers |
| 6,558,321 B1 | 5/2003 | Burd et al. |
| 6,558,994 B2 | 5/2003 | Cha et al. |
| 6,573,563 B2 | 6/2003 | Lee et al. |
| 6,582,462 B1 | 6/2003 | Andersen et al. |
| 6,599,250 B2 | 7/2003 | Webb et al. |
| 6,605,112 B1 | 8/2003 | Moll et al. |
| 6,629,534 B1 | 10/2003 | St. Goar et al. |
| 6,640,137 B2 | 10/2003 | MacDonald |
| 6,641,610 B2 | 11/2003 | Wolf et al. |
| 6,645,143 B2 | 11/2003 | VanTassel et al. |
| 6,673,109 B2 | 1/2004 | Cox |
| 6,678,561 B2 | 1/2004 | Forsell et al. |
| 6,682,480 B1 | 1/2004 | Habib et al. |
| 6,682,503 B1 | 1/2004 | Fariss et al. |
| 6,682,559 B2 | 1/2004 | Myers et al. |
| 6,695,866 B1 | 2/2004 | Kuehn et al. |
| 6,709,385 B2 | 3/2004 | Forsell et al. |
| 6,718,200 B2 | 4/2004 | Marmaropoulos et al. |
| 6,719,787 B2 | 4/2004 | Cox |
| 6,719,788 B2 | 4/2004 | Cox |
| 6,719,789 B2 | 4/2004 | Cox |
| 6,731,976 B2 | 5/2004 | Penn et al. |
| 6,733,525 B2 | 5/2004 | Yang et al. |
| 6,736,846 B2 | 5/2004 | Cox |
| 6,752,813 B2 | 6/2004 | Goldfarb et al. |
| 6,796,942 B1 | 9/2004 | Kreiner et al. |
| 6,822,343 B2 | 11/2004 | Estevez |
| 6,851,628 B1 | 2/2005 | Garrison et al. |
| 6,855,115 B2 | 2/2005 | Fonseca et al. |
| 6,889,772 B2 | 5/2005 | Buytaert et al. |
| 6,890,300 B2 | 5/2005 | Lloyd et al. |
| 6,896,651 B2 | 5/2005 | Gross et al. |
| 6,896,690 B1 | 5/2005 | Lambrecht et al. |
| 6,913,600 B2 | 7/2005 | Valley et al. |

| Patent/Publication | Date | Name |
|---|---|---|
| 6,915,165 B2 | 7/2005 | Forsell et al. |
| 6,926,246 B2 | 8/2005 | Ginggen et al. |
| 6,929,653 B2 | 8/2005 | Strecter |
| 6,932,792 B1 | 8/2005 | St. Goar et al. |
| 6,951,229 B2 | 10/2005 | Garrison et al. |
| 6,951,571 B1 | 10/2005 | Srivastava |
| 6,953,429 B2 | 10/2005 | Forsell et al. |
| 6,961,619 B2 | 11/2005 | Casey |
| 6,970,742 B2 | 11/2005 | Mann et al. |
| 6,979,350 B2 | 12/2005 | Moll et al. |
| 6,985,078 B2 | 1/2006 | Suzuki et al. |
| 6,989,027 B2 | 1/2006 | Allen et al. |
| 7,011,095 B2 | 3/2006 | Wolf et al. |
| 7,011,624 B2 | 3/2006 | Forsell et al. |
| 7,017,583 B2 | 3/2006 | Forsell et al. |
| 7,018,406 B2 | 3/2006 | Seguin et al. |
| 7,021,402 B2 | 4/2006 | Beato et al. |
| 7,025,727 B2 | 4/2006 | Brockway et al. |
| 7,044,920 B2 | 5/2006 | Letort et al. |
| 7,060,080 B2 | 6/2006 | Bachmann et al. |
| 7,081,683 B2 | 7/2006 | Ariav et al. |
| 7,109,933 B2 | 9/2006 | Ito et al. |
| 7,131,447 B2 | 11/2006 | Sterman et al. |
| 7,131,945 B2 | 11/2006 | Fink et al. |
| 7,134,580 B2 | 11/2006 | Garrison et al. |
| 7,144,400 B2 | 12/2006 | Byrum et al. |
| 7,147,640 B2 | 12/2006 | Huebner et al. |
| 7,153,262 B2 | 12/2006 | Stivoric et al. |
| 7,187,978 B2 | 3/2007 | Malek et al. |
| 7,225,032 B2 | 5/2007 | Schmeling et al. |
| 7,257,438 B2 | 8/2007 | Kinast |
| 7,285,090 B2 | 10/2007 | Stivoric et al. |
| 7,383,071 B1 * | 6/2008 | Russell et al. .................. 600/345 |
| 2001/0011543 A1 | 8/2001 | Forsell |
| 2001/0041823 A1 | 11/2001 | Snyder et al. |
| 2002/0049394 A1 | 4/2002 | Roy et al. |
| 2002/0120200 A1 | 8/2002 | Brockway et al. |
| 2002/0137991 A1 * | 9/2002 | Scarantino et al. ........... 600/300 |
| 2002/0138009 A1 | 9/2002 | Brockway et al. |
| 2002/0177782 A1 | 11/2002 | Penner |
| 2003/0009201 A1 | 1/2003 | Forsell |
| 2003/0030893 A1 | 2/2003 | Cornelius et al. |
| 2003/0032857 A1 | 2/2003 | Forsell |
| 2003/0037591 A1 | 2/2003 | Ashton et al. |
| 2003/0045775 A1 | 3/2003 | Forsell |
| 2003/0066536 A1 | 4/2003 | Forsell |
| 2003/0088148 A1 | 5/2003 | Forsell |
| 2003/0092962 A1 | 5/2003 | Forsell |
| 2003/0093117 A1 | 5/2003 | Saadat |
| 2003/0100929 A1 | 5/2003 | Forsell |
| 2003/0105385 A1 | 6/2003 | Forsell |
| 2003/0109771 A1 | 6/2003 | Forsell |
| 2003/0114729 A1 | 6/2003 | Forsell |
| 2003/0125605 A1 | 7/2003 | Forsell |
| 2003/0125768 A1 | 7/2003 | Peter |
| 2003/0135089 A1 | 7/2003 | Forsell |
| 2003/0135090 A1 | 7/2003 | Forsell |
| 2003/0136417 A1 | 7/2003 | Fonseca et al. |
| 2003/0144648 A1 | 7/2003 | Forsell |
| 2003/0163079 A1 | 8/2003 | Burnett |
| 2003/0216666 A1 | 11/2003 | Ericson et al. |
| 2004/0054352 A1 | 3/2004 | Adams et al. |
| 2004/0113790 A1 | 6/2004 | Hamel et al. |
| 2004/0133092 A1 | 7/2004 | Kain |
| 2004/0147969 A1 | 7/2004 | Mann et al. |
| 2004/0172087 A1 | 9/2004 | Forsell |
| 2004/0186396 A1 | 9/2004 | Roy et al. |
| 2004/0254537 A1 | 12/2004 | Conlon et al. |
| 2005/0015014 A1 | 1/2005 | Fonseca et al. |
| 2005/0025979 A1 | 2/2005 | Sandt et al. |
| 2005/0027175 A1 | 2/2005 | Yang |
| 2005/0038328 A1 | 2/2005 | Stoehrer et al. |
| 2005/0061079 A1 | 3/2005 | Schulman |
| 2005/0102026 A1 | 5/2005 | Turner et al. |
| 2005/0159789 A1 | 7/2005 | Brockway et al. |
| 2005/0165317 A1 | 7/2005 | Turner et al. |
| 2005/0182330 A1 | 8/2005 | Brockway et al. |
| 2005/0187482 A1 | 8/2005 | O'Brien et al. |
| 2005/0187488 A1 | 8/2005 | Wolf |
| 2005/0192642 A1 | 9/2005 | Forsell |
| 2005/0240155 A1 | 10/2005 | Conlon |
| 2005/0240156 A1 | 10/2005 | Conlon |
| 2005/0250979 A1 | 11/2005 | Coe |
| 2005/0267406 A1 | 12/2005 | Hassler |
| 2005/0267500 A1 | 12/2005 | Hassler et al. |
| 2005/0272968 A1 | 12/2005 | Byrum et al. |
| 2005/0277960 A1 | 12/2005 | Hassler et al. |
| 2005/0277974 A1 | 12/2005 | Hassler et al. |
| 2005/0283172 A1 * | 12/2005 | Conlon ......................... 606/153 |
| 2005/0288604 A1 | 12/2005 | Eigler et al. |
| 2005/0288720 A1 | 12/2005 | Ross et al. |
| 2005/0288721 A1 | 12/2005 | Girouard et al. |
| 2005/0288739 A1 | 12/2005 | Hassler et al. |
| 2005/0288740 A1 | 12/2005 | Hassler et al. |
| 2005/0288741 A1 | 12/2005 | Hassler et al. |
| 2005/0288742 A1 | 12/2005 | Giordano et al. |
| 2006/0002035 A1 | 1/2006 | Gao et al. |
| 2006/0010090 A1 | 1/2006 | Brockway et al. |
| 2006/0020224 A1 | 1/2006 | Geiger |
| 2006/0020305 A1 | 1/2006 | Desai et al. |
| 2006/0035446 A1 | 2/2006 | Chang et al. |
| 2006/0047205 A1 | 3/2006 | Ludomirsky et al. |
| 2006/0049714 A1 | 3/2006 | Liu et al. |
| 2006/0058627 A1 | 3/2006 | Flaherty et al. |
| 2006/0064134 A1 | 3/2006 | Mazar et al. |
| 2006/0085051 A1 | 4/2006 | Fritsch |
| 2006/0089571 A1 | 4/2006 | Gertner |
| 2006/0094966 A1 | 5/2006 | Brockway et al. |
| 2006/0100531 A1 | 5/2006 | Moser |
| 2006/0113187 A1 | 6/2006 | Deng et al. |
| 2006/0122285 A1 | 6/2006 | Falloon et al. |
| 2006/0122863 A1 | 6/2006 | Gottesman et al. |
| 2006/0142635 A1 | 6/2006 | Forsell |
| 2006/0149124 A1 | 7/2006 | Forsell |
| 2006/0149324 A1 | 7/2006 | Mann et al. |
| 2006/0149327 A1 | 7/2006 | Hedberg et al. |
| 2006/0157701 A1 | 7/2006 | Bauer et al. |
| 2006/0161186 A1 | 7/2006 | Hassler et al. |
| 2006/0178617 A1 | 8/2006 | Adams et al. |
| 2006/0178695 A1 | 8/2006 | Decant et al. |
| 2006/0183967 A1 | 8/2006 | Lechner |
| 2006/0184206 A1 | 8/2006 | Baker et al. |
| 2006/0189887 A1 | 8/2006 | Hassler et al. |
| 2006/0189888 A1 | 8/2006 | Hassler et al. |
| 2006/0189889 A1 | 8/2006 | Gertner |
| 2006/0199997 A1 | 9/2006 | Hassler et al. |
| 2006/0211912 A1 | 9/2006 | Dlugos et al. |
| 2006/0211913 A1 | 9/2006 | Dlugos et al. |
| 2006/0211914 A1 | 9/2006 | Hassler et al. |
| 2006/0217668 A1 | 9/2006 | Schulze et al. |
| 2006/0217673 A1 | 9/2006 | Schulze et al. |
| 2006/0235310 A1 | 10/2006 | O'Brien et al. |
| 2006/0235439 A1 | 10/2006 | Molitor et al. |
| 2006/0235448 A1 | 10/2006 | Roslin et al. |
| 2006/0244914 A1 | 11/2006 | Cech et al. |
| 2006/0247682 A1 | 11/2006 | Gerber et al. |
| 2006/0247719 A1 | 11/2006 | Maschino et al. |
| 2006/0247722 A1 | 11/2006 | Maschino et al. |
| 2006/0247723 A1 | 11/2006 | Gerber et al. |
| 2006/0247724 A1 | 11/2006 | Gerber et al. |
| 2006/0247725 A1 | 11/2006 | Gerber et al. |
| 2006/0252982 A1 | 11/2006 | Hassler et al. |
| 2006/0293625 A1 | 12/2006 | Hunt et al. |
| 2006/0293626 A1 | 12/2006 | Byrum et al. |
| 2006/0293627 A1 | 12/2006 | Byrum et al. |
| 2007/0010790 A1 | 1/2007 | Byrum et al. |
| 2007/0027356 A1 | 2/2007 | Ortiz |
| 2007/0027493 A1 | 2/2007 | Ben-Haim et al. |
| 2007/0067206 A1 | 3/2007 | Haggerty et al. |
| 2007/0070906 A1 | 3/2007 | Thakur |
| 2007/0072452 A1 | 3/2007 | Inagaki et al. |
| 2007/0081304 A1 | 4/2007 | Takeguchi |
| 2007/0156013 A1 | 7/2007 | Birk |
| 2007/0167672 A1 | 7/2007 | Dlugos et al. |
| 2007/0173881 A1 | 7/2007 | Birk et al. |
| 2007/0179583 A1 | 8/2007 | Goetzinger et al. |
| 2007/0208313 A1 | 9/2007 | Conlon et al. |

| | | | | | | |
|---|---|---|---|---|---|---|
| 2007/0225781 | A1 | 9/2007 | Saadat et al. | WO | WO-9511057 | 4/1995 |
| 2007/0280851 | A1* | 12/2007 | Freeman et al. ............ 422/1 | WO | WO-9715351 | 5/1997 |
| 2008/0009680 | A1 | 1/2008 | Hassler | WO | WO-9733513 | 9/1997 |

FOREIGN PATENT DOCUMENTS

| | | | | | |
|---|---|---|---|---|---|
| WO | WO-9833554 | 8/1998 | | | |
| WO | WO-9835610 | 8/1998 | | | |
| CA | 1119469 | 3/1982 | WO | WO-9901063 | 1/1999 |
| CA | 1275135 | 10/1990 | WO | WO-9918850 | 4/1999 |
| CA | 1277885 | 12/1990 | WO | WO-0004945 | 2/2000 |
| CA | 1317482 | 5/1993 | WO | WO-0033738 | 6/2000 |
| CA | 2082015 | 5/1993 | WO | WO-0072899 | 12/2000 |
| CA | 1327191 | 2/1994 | WO | WO-0104487 | 1/2001 |
| CA | 2119101 | 9/1994 | WO | WO-0112075 | 2/2001 |
| CA | 2305998 | 4/1999 | WO | WO-0112076 | 2/2001 |
| CN | 1059035 | 2/1992 | WO | WO-0112077 | 2/2001 |
| CN | 1119469 | 3/1996 | WO | WO-0112078 | 2/2001 |
| CN | 1241003 | 1/2000 | WO | WO-0121066 | 3/2001 |
| EA | 4581 | 6/2004 | WO | WO-0136014 | 5/2001 |
| EP | 125387 B1 | 11/1984 | WO | WO-0145485 | 6/2001 |
| EP | 417171 | 3/1991 | WO | WO-0145486 | 6/2001 |
| EP | 508141 | 10/1992 | WO | WO-0147431 | 7/2001 |
| EP | 568730 | 11/1993 | WO | WO-0147432 | 7/2001 |
| EP | 605302 | 7/1994 | WO | WO-0147433 | 7/2001 |
| EP | 660482 | 6/1995 | WO | WO-0147434 | 7/2001 |
| EP | 714017 | 5/1996 | WO | WO-0147435 | 7/2001 |
| EP | 769340 | 4/1997 | WO | WO-0147440 | 7/2001 |
| EP | 846475 | 6/1998 | WO | WO-0147575 | 7/2001 |
| EP | 848780 | 6/1998 | WO | WO-0148451 | 7/2001 |
| EP | 876808 | 11/1998 | WO | WO-0149245 | 7/2001 |
| EP | 888079 | 1/1999 | WO | WO-0150832 | 7/2001 |
| EP | 914059 | 5/1999 | WO | WO-0150833 | 7/2001 |
| EP | 981293 | 3/2000 | WO | WO-0154626 | 8/2001 |
| EP | 997680 | 5/2000 | WO | WO-0158388 | 8/2001 |
| EP | 1003021 | 5/2000 | WO | WO-0158390 | 8/2001 |
| EP | 1022983 | 8/2000 | WO | WO-0158391 | 8/2001 |
| EP | 1050265 | 11/2000 | WO | WO-0158393 | 8/2001 |
| EP | 1115329 | 7/2001 | WO | WO-0160453 | 8/2001 |
| EP | 1119314 | 8/2001 | WO | WO-0181890 | 11/2001 |
| EP | 1128871 | 9/2001 | WO | WO-0200118 | 1/2002 |
| EP | 1202674 | 5/2002 | WO | WO-0215769 | 2/2002 |
| EP | 1213991 | 6/2002 | WO | WO-0226161 | 4/2002 |
| EP | 1253877 | 11/2002 | WO | WO-02053228 | 7/2002 |
| EP | 1253879 | 11/2002 | WO | WO-02055126 | 7/2002 |
| EP | 1253880 | 11/2002 | WO | WO-02058551 | 8/2002 |
| EP | 1253881 | 11/2002 | WO | WO-02065894 | 8/2002 |
| EP | 1253883 | 11/2002 | WO | WO-02076289 | 10/2002 |
| EP | 1253888 | 11/2002 | WO | WO-02082984 | 10/2002 |
| EP | 1255511 | 11/2002 | WO | WO-02089655 | 11/2002 |
| EP | 1255513 | 11/2002 | WO | WO-02090894 | 11/2002 |
| EP | 1255514 | 11/2002 | WO | WO-02100481 | 12/2002 |
| EP | 1263355 | 12/2002 | WO | WO-03002192 | 1/2003 |
| EP | 1263357 | 12/2002 | WO | WO-03002193 | 1/2003 |
| EP | 1284691 | 2/2003 | WO | WO-03020182 | 3/2003 |
| EP | 1374758 | 1/2004 | WO | WO-03061467 | 7/2003 |
| EP | 1488735 | 12/2004 | WO | WO-03061504 | 7/2003 |
| EP | 1500411 | 1/2005 | WO | WO-03096889 | 11/2003 |
| EP | 1510306 | 3/2005 | WO | WO-2004014456 | 2/2004 |
| EP | 1518514 | 3/2005 | WO | WO-2004019773 | 3/2004 |
| EP | 1545303 | 6/2005 | WO | WO-2004058101 | 7/2004 |
| EP | 1547549 | 6/2005 | WO | WO-2004066879 | 8/2004 |
| EP | 1563814 | 8/2005 | WO | WO-2004110263 | 12/2004 |
| EP | 1568338 | 8/2005 | WO | WO-2005000206 | 1/2005 |
| EP | 1582175 | 10/2005 | WO | WO-2005007075 | 1/2005 |
| EP | 1582176 | 10/2005 | WO | WO-2005107583 | 11/2005 |
| EP | 1584303 | 10/2005 | WO | WO-2006001851 | 1/2006 |
| EP | 1586283 | 10/2005 | WO | WO-2006035446 | 4/2006 |
| EP | 1591086 | 11/2005 | WO | WO-2006113187 | 10/2006 |
| EP | 1593359 | 11/2005 | WO | WO-2006122285 | 11/2006 |
| EP | 1598030 | 11/2005 | WO | WO-2007067206 | 6/2007 |
| EP | 1609440 | 12/2005 | WO | WO-2007070906 | 6/2007 |
| EP | 1674033 | 6/2006 | WO | WO-2007072452 | 6/2007 |
| EP | 1736123 | 12/2006 | WO | WO-2007081304 | 7/2007 |
| EP | 1799119 | 6/2007 | WO | WO-2007104356 | 9/2007 |
| GB | 2355937 | 5/2001 | | | |
| WO | WO-8911244 | 11/1989 | | | |
| WO | WO-8911701 | 11/1989 | | | |
| WO | WO-9004368 | 5/1990 | | | |

OTHER PUBLICATIONS

"Rad Hard Aerospace Components Products", Honeywell product and service information from website http://www.honeywell.com/sites/portal?smap=aerospace&page=Radiation-Hardened-Electronics3&theme=T6&catID=C815147E4-8786-29FE-49EB-C21C8790AA99&id=H0166BA51-5344-E57E-5C37-C6333EA43F61&sel=1; 1 page.

"Radiation Hardened Electronics and Radiation Technology", Honeywell product and service information from website http://www.honeywell.com/sites/portal?smap=aerospace&page=Radiation-Hardened-Electronics&theme=T4; 2 pages.

Kirchner, G., "Honeywell and Synopsys: Concept-to-Parts Solutions for Next Generation Rad-Hard ASICs", in online magazine Compiler, http://www.synopsys.com/news/pubs/compiler/artlead_redasic-apr05.html, Apr. 2005, 5 pages.

P.A. Neukomm and H. Kundig, "Passive Wireless Actuator Control and Sensor Signal Transmission," Sensors and Actuators, A21-A23 (1990) 258-262.

* cited by examiner

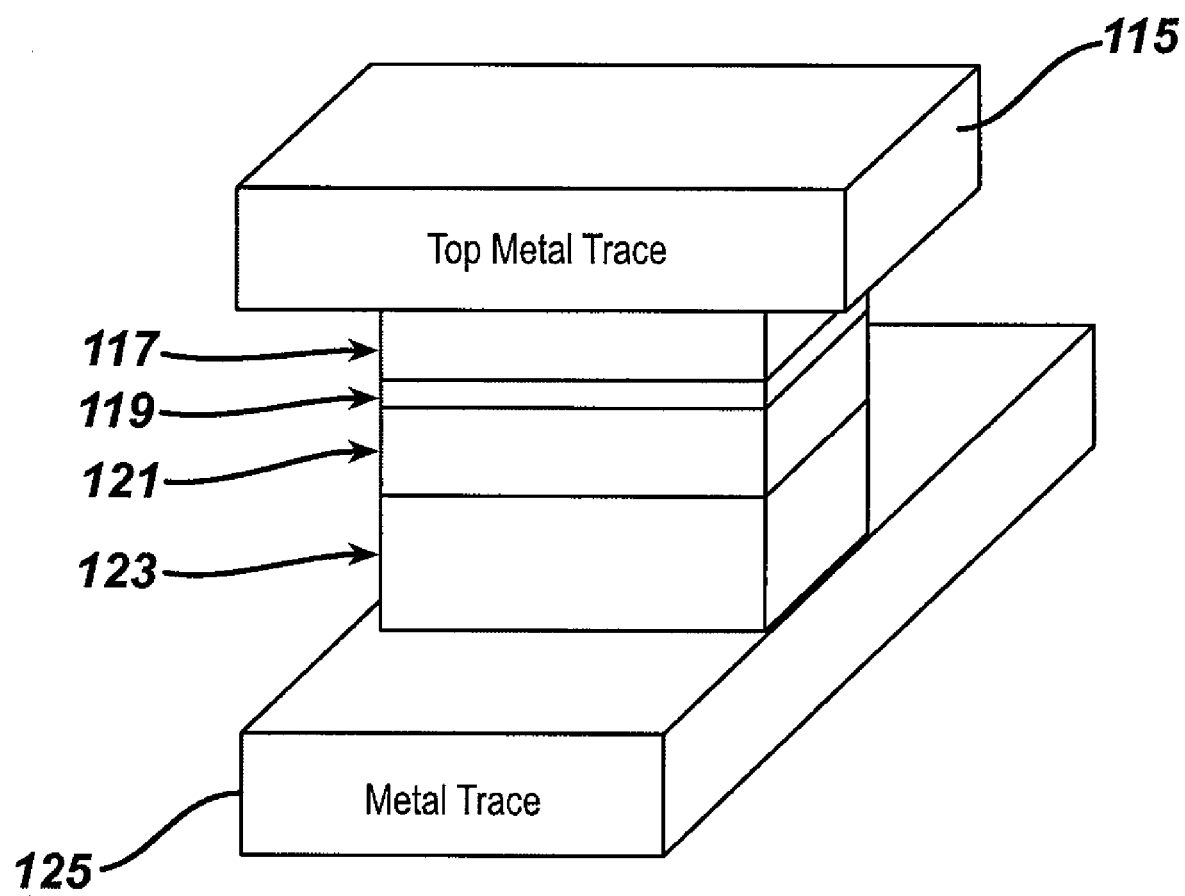

SYSTEM AND METHOD OF STERILIZING AN IMPLANTABLE MEDICAL DEVICE

FIELD

The present disclosure relates to an implantable medical device and system, in particular to an implantable medical device having internal circuitry capable of withstanding some pre-determined amount of sterilization radiation.

BACKGROUND

Obesity is becoming a growing concern, particularly in the United States, as the number of obese people continues to increase, and more is learned about the negative health effects of obesity. Morbid obesity, in which a person is 100 pounds or more over ideal body weight, in particular poses significant risks for severe health problems. Accordingly, a great deal of attention is being focused on treating obese patients. One method of treating morbid obesity has been to place a restriction device, such as an elongated band, about the upper portion of the stomach. Gastric bands have typically comprised a fluid-filled elastomeric balloon with fixed endpoints that encircles the stomach just inferior to the esophageal-gastric junction to form a small gastric pouch above the band and a reduced stoma opening in the stomach. When fluid is infused into the balloon, the band expands against the stomach creating a food intake restriction or stoma in the stomach. To decrease this restriction, fluid is removed from the band. The effect of the band is to reduce the available stomach volume and thus the amount of food that can be consumed before becoming "full."

Food restriction devices have also comprised mechanically adjusted bands that similarly encircle the upper portion of the stomach. These bands include any number of resilient materials or gearing devices, as well as drive members, for adjusting the bands. Additionally, gastric bands have been developed that include both hydraulic and mechanical drive elements. An example of such an adjustable gastric band is disclosed in U.S. Pat. No. 6,067,991, entitled "Mechanical Food Intake Restriction Device" which issued on May 30, 2000, and is incorporated herein by reference. It is also known to restrict the available food volume in the stomach cavity by implanting an inflatable elastomeric balloon within the stomach cavity itself. The balloon is filled with a fluid to expand against the stomach walls and, thereby, decrease the available food volume within the stomach.

With each of the above-described food restriction devices, safe, effective treatment requires that the device be regularly monitored and adjusted to vary the degree of restriction applied to the stomach. With banding devices, the gastric pouch above the band will substantially increase in size following the initial implantation. Accordingly, the stoma opening in the stomach must initially be made large enough to enable the patient to receive adequate nutrition while the stomach adapts to the banding device. As the gastric pouch increases in size, the band may be adjusted to vary the stoma size. In addition, it is desirable to vary the stoma size in order to accommodate changes in the patient's body or treatment regime, or in a more urgent case, to relieve an obstruction or severe esophageal dilatation. Traditionally, adjusting a hydraulic gastric band required a scheduled clinician visit during which a Huber needle and syringe were used to penetrate the patient's skin and add or remove fluid from the balloon via an injection port. More recently, implantable pumps have been developed which enable non-invasive adjustments of the band. An external programmer communicates with the implanted pump using telemetry to control the pump. During a scheduled visit, a physician places a handheld portion of the programmer near the gastric implant and transmits power and command signals to the implant. The implant in turn adjusts the fluid levels in the band and transmits a response command to the programmer.

Implants such as those described above include electronics for data storage, data transfer, power, and the like. For example, such devices may be internally powered by a battery or capacitor while others may be powered by an externally coupled power source or passive telemetry system. Often, such internal circuitry can be adversely affected when subjected to an external energy source. For example, application of sterilization radiation can adversely affect the circuitry, and ultimately result in system failure. As radiation sterilization is a desirable from both an economic, environmental, and performance perspective, there remains a need for a system and method capable of withstanding radiation supplied during a sterilization procedure.

SUMMARY

An implantable medical device and system having internal circuitry configured to withstand a pre-determined amount of radiation, including the amount of radiation encountered during a sterilization procedure, is provided. In general, the system includes an internal control module in electrical communication with an implantable medical device which is configured to be disposed in a patient's peritoneal cavity. For example, the medical device can be an implantable restriction device configured to form a restriction in a pathway. The internal control module can include a circuit board, individual components, and/or any number of integrated circuits (e.g., application specific integrated circuits) wherein the circuitry, or at least some portion thereof, is fabricated so as to withstand some amount of radiation For example, some portion of the circuitry can be fabricated utilizing a radiation compliant material (e.g., a ceramic material, titanium, gold, silver, tantalum, platinum, palladium, rhodium. etc.). Further, the circuitry can be fabricated (at least in part) from gallium arsenide. Also, at least some portion of the circuitry can be fabricated utilizing silicon-on-insulator ("SOI") technology. Additionally, the circuitry can include various components which are inherently resistant to such radiation (e.g., Magnetoresistive Random Access Memory).

Various aspects of an implantable medical device and system having internal circuitry capable of resisting a pre-determined amount of radiation are provided. In one such aspect, the system includes an implantable medical device configured to be disposed within a patient's peritoneal cavity. For example, the implantable device can be an implantable restriction device configured to form a restriction in a pathway. Additionally, the system includes an internal control module in electrical communication with at least one of the implantable medical device and an external device wherein the control module can include circuitry components resistant to an amount of radiation (e.g., the amount of radiation encountered during sterilization of the implantable device). The circuitry components (which can be present in any of a sensor, a microprocessor, a microcontroller, signal conditioning circuitry, a gate array, an application specific integrated circuit, a memory device, a magnetic random access memory, a magnetic control circuit, an acoustical wave device, a circuit board, etc.) can be fabricated in various manners so as to resist such radiation (i.e., be functional following exposure to radiation such as for purposes of sterilization). For example, at least one of the circuitry components can be fabricated at least in part from a radiation compliant material. Such materials can include a ceramic material, titanium, gold, silver, tantalum, platinum, palladium, rhodium, etc. Additionally, in some embodiments at least one of the circuitry components can be fabricated at least in part from gallium arsenide. In one embodiment, at least one of the circuitry components can be fabricated utilizing silicon-on-insulator technology. For example, the circuitry components can include at least one silicon layer having a top face and a bottom face, and the circuitry components can further include at least one insulator layer disposed on at least one face of the silicon layer. The insulator layer can include various materials. For example, the insulator layer can include sapphire, silicon dioxide, etc.

The components of the system can be resistant to various types and/or doses of radiation. In an exemplary embodiment, the circuitry components can be resistant to an amount of radiation encountered during a gamma radiation process. The sterilization radiation for a single dose can be any amount of up to about 50 kilogray (kGy) (e.g., in a range of about 25 kilogray (kGy) to about 50 kGy). Additionally, the components can also be configured to withstand additional doses of about 25 kGy to about 50 kGy, up to a total of about 100 kGy or higher if desired. Lower doses of radiation (e.g., below 25 kGy) may be used when the manufacturing environmental conditions are highly controlled. As indicated, various types of radiation can also be utilized. For example, the radiation can be gamma radiation, x-ray radiation, electron beam radiation, etc.

In another aspect, an implantable medical system is provided which includes an implantable medical device configured to be disposed within a patient's peritoneal cavity, and an implantable control module having a plurality of electronic components (e.g., a surface acoustical wave device) that are configured to be resistant to a pre-determined dose of radiation (e.g., gamma radiation, x-ray radiation, electron beam radiation). In an exemplary embodiment, the pre-determined dose of radiation is gamma radiation capable of sterilizing the implantable medical device. While various doses of radiation are within the spirit and scope of the present disclosure, in an exemplary embodiment the pre-determined dose of radiation is any amount up to about 50 kGy. Additionally, the components can also be configured to withstand additional doses of about 25 kGy to about 50 kGy, up to a total of about 100 kGy or higher if desired. The electronic components can be fabricated in various manners so as to be resistant to radiation. For example, at least one of the electronic components can be fabricated utilizing silicon-on-insulator technology. Utilizing such technology, the electronic components can include at least one silicon layer having a top face and a bottom face, and the electronic components can further include at least one insulator layer disposed on at least one face of the silicon layer. Also, the electronic components can be fabricated at least in part from a radiation compliant material.

Additionally, various aspects of a method for sterilizing an implantable medical device are provided. In one such aspect, the method includes providing an implantable medical device configured to be disposed within a patient's peritoneal cavity. For example, the implantable device can be an implantable restriction device configured to form a restriction in a pathway. The implantable device includes an internal control module with any number of electronic components configured to be resistant to a pre-determined dose of radiation. Further, the method includes delivering a pre-determined dose of radiation to the implantable medical device. The electronic components can be configured and/or fabricated in various manners so as to exhibit such radiation resistance. For example, the electronic components can be fabricated utilizing silicon-on-insulator technology, fabricated at least in part from radiation compliant materials, fabricated at least in part from gallium arsenide, etc.

The pre-determined dose of radiation can include any type and/or amount of radiation capable of providing a desired effect (e.g., sterilizing the implantable medical device). For example, the radiation can be gamma radiation, x-ray radiation, electron beam radiation, etc. Additionally, the radiation can be delivered in various amounts. For example, the radiation can be delivered in an amount up to about 50 kGy. Further, the method can include delivering at least one additional dose of a pre-determined amount of radiation. For example, the method can include the application of additional doses of about 25 kGy to about 50 kGy, up to a total of about 100 kGy or higher if desired.

BRIEF DESCRIPTION OF THE DRAWINGS

The present disclosure will be more fully understood from the following detailed description taken in conjunction with the accompanying drawings, in which:

FIG. 10A is a representation of internal circuitry including Magnetic Random Access Memory ("MRAM")

DETAILED DESCRIPTION

Certain exemplary embodiments will now be described to provide an overall understanding of the principles of the structure, function, manufacture, and use of the devices, systems, and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present disclosure is defined solely by the claims. The features illustrated or described in connection with one exemplary embodiment may be combined with the features of other embodiments. Such modifications and variations are intended to be included within the scope of the present disclosure.

An implantable medical device and system having internal circuitry configured to withstand a pre-determined amount of radiation is provided. The amount of radiation can be any amount, type (e.g., gamma radiation, x-ray radiation, electron beam radiation), and/or dosage as desired to provide the desired therapeutic effect (e.g., sterilization). For example, the internal circuitry can be capable of withstanding a dosage of radiation in an amount up to about 100 kilogray ("kGy"), including a single dose in a range of about 25 kGy to about 50 kGy. As will be described, the internal circuitry can be configured to withstand such desired amounts of radiation in various manners. For example, some portion of the circuitry (e.g., a circuit board, an integrated circuit, individual component, etc.) can be fabricated at least in part utilizing a wide range of radiation compliant materials (e.g., a ceramic material, titanium, gold, silver, tantalum, platinum, palladium, and rhodium). Additionally, the circuitry can be fabricated utilizing gallium arsenide. Further, some portion of the circuitry can be fabricated utilizing silicon-on-insulator ("SOI") technology which allows, for example, various components of an integrated circuit to be electrically isolated from one another by the presence of an insulator material (e.g., sapphire) deposited on a typical silicon substrate. Additionally, the circuitry can include components which are inherently resistant to some degree of radiation. For example, such components can include Magnetoresistive Random Access Memory ("MRAM"), surface acoustical wave devices, etc. Thus, such radiation hardening provides the implantable system with effective radiation resistance to the desired sterilization procedure.

Figure 1A:
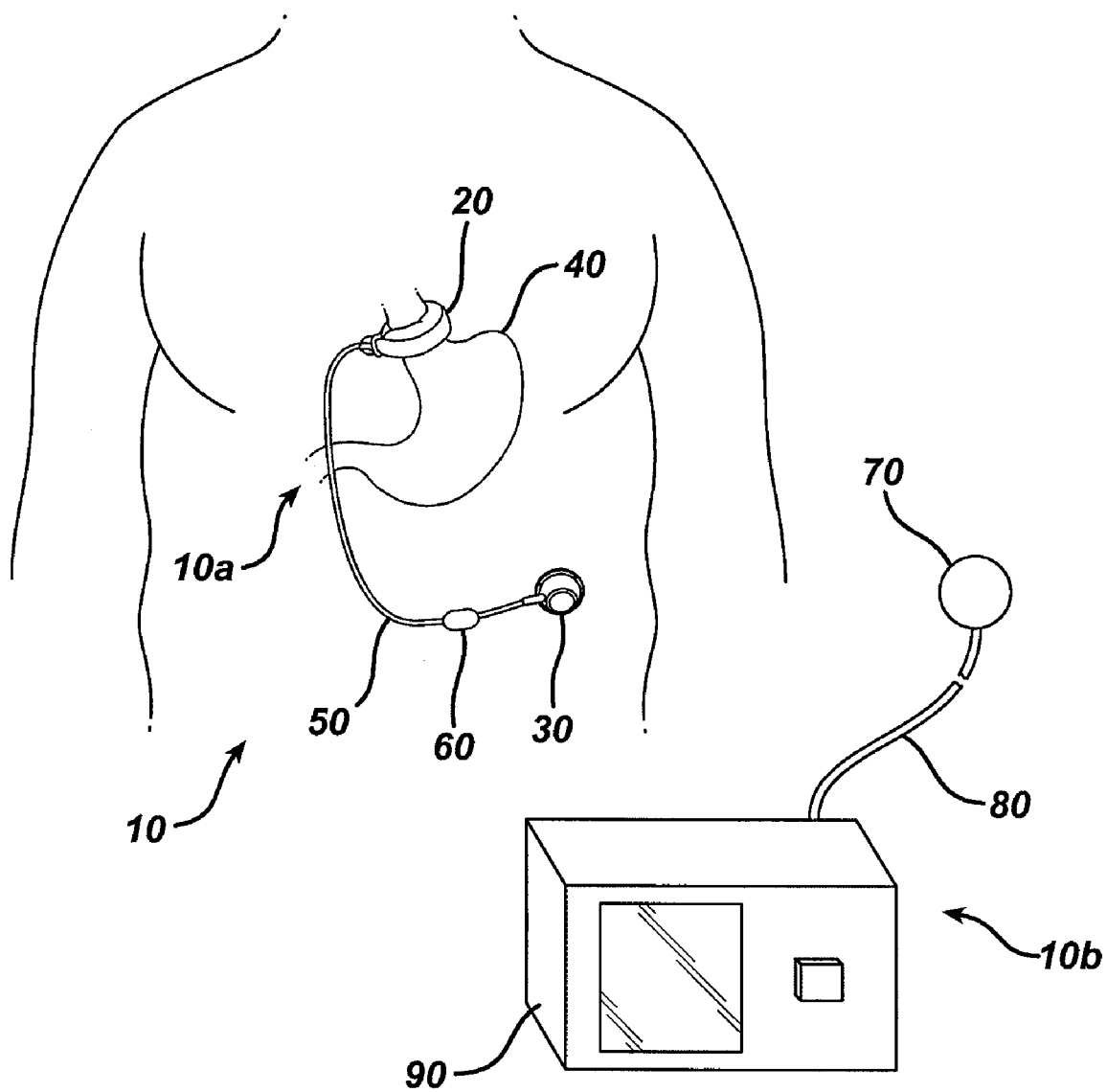
FIG. 1A is a perspective view of one embodiment of a food intake restriction system.
Figure 1B:
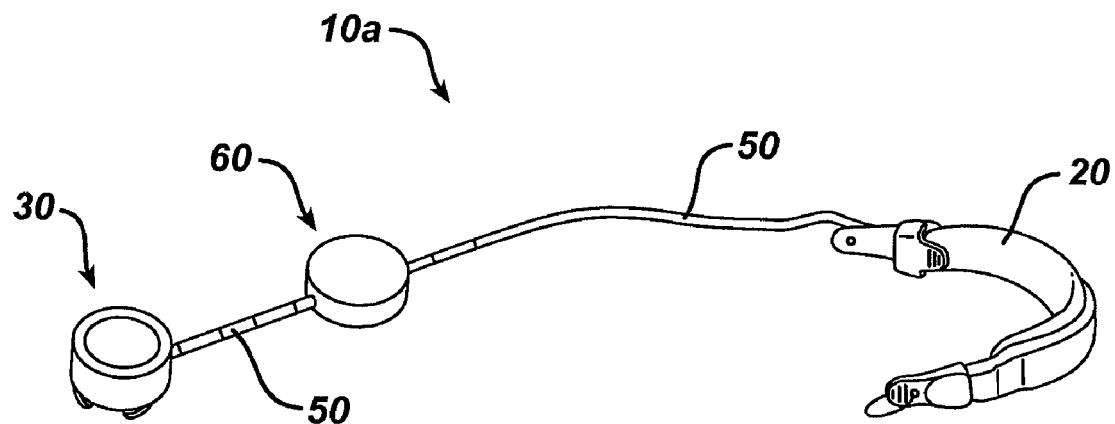
FIG. 1B is perspective view of one embodiment of a restriction system.

As will be appreciated by those skilled in the art, various embodiments of an implantable medical device and system are within the spirit and scope of the present disclosure. In an exemplary embodiment, the implantable system includes an implantable medical device configured to be disposed within a patient's peritoneal cavity. For example, the implantable medical device can be an implantable restriction device which is configured to form a restriction in a pathway. FIG. 1A illustrates one exemplary embodiment of a food intake restriction system 10. As shown, the system 10 generally includes an implantable portion 10a and an external portion 10b. FIG. 1B illustrates the implantable portion 10a outside of a patient. As shown, the implantable portion 10a includes an adjustable gastric band 20 that is configured to be positioned around the upper portion of a patient's stomach 40 and an injection port housing 30 that is fluidly coupled to the adjustable gastric band 20, e.g., via a catheter 50. The injection port 30 can be configured to allow fluid to be introduced into and removed from the gastric band 20 to thereby adjust the size of the band 20 and thus the pressure applied to the stomach 40. The injection port 30 can thus be implanted at a location within the body that is accessible through tissue. Typically, injection ports are positioned in the lateral subcostal region of the patient's abdomen under the skin and layers of fatty tissue. Surgeons also typically implant injection ports on the sternum of the patient.

The internal portion 10a can also include a sensing or measuring device that is in fluid communication with the closed fluid circuit in the implantable portion 10a. In one embodiment, the sensing device is a pressure sensing device configured to measure the fluid pressure of the closed fluid circuit. While the pressure measuring device can have various configurations and can be positioned anywhere along the internal portion 10a, including within the injection port 30, in the illustrated embodiment the pressure measuring device is in the form of a pressure sensor that is disposed within a sensor housing 60 positioned adjacent to the injection port 30. The catheter 50 can include a first portion that is coupled between the gastric band 20 and the pressure sensor housing 60 and a second portion that is coupled between the pressure sensor housing 60 and the injection port 30. While it is understood that the sensing device can be configured to obtain data relating to one or more relevant parameters, generally it will be described herein in a context of a pressure sensing device.

As further shown in FIG. 1A, the external portion 10b generally includes a data reading device 70 that is configured to be positioned on the skin surface above the pressure sensor housing 60 (which can be implanted beneath thick tissue, e.g., over 10 cm thick) to non-invasively communicate with the pressure sensor housing 60 and thereby obtain pressure measurements. The data reading device 70 can optionally be electrically coupled (wirelessly or wired, as in this embodiment via an electrical cable assembly 80) to a control box 90 that can display the pressure measurements, other data obtained from the data reading device 70, and/or data alerts. While shown in this example as being local to the patient, the control box 90 can be at a location local to or remote from the patient.

Figure 2A:
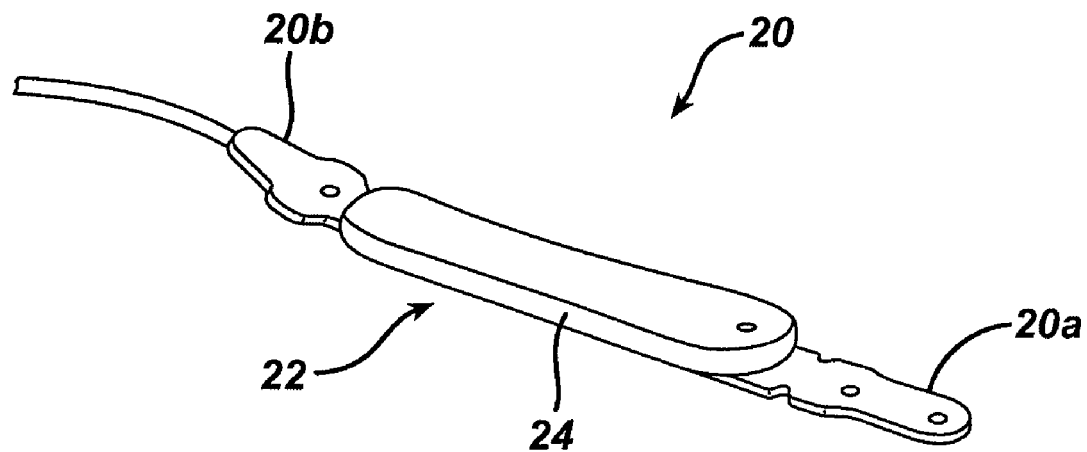
FIG. 2A is a perspective view of the gastric band of the restriction system shown in FIG. 1B.

FIG. 2A shows the gastric band 20 in more detail. While the gastric band 20 can have a variety of configurations, and various gastric bands currently known in the art can be used with the present disclosure, in the illustrated embodiment the gastric band 20 has a generally elongate shape with a support structure 22 having first and second opposite ends 20a, 20b that can be formed in a loop such that the ends are secured to each other. Various mating techniques can be used to secure the ends 20a, 20b to one another. In the illustrated embodiment, the ends 20a, 20b are in the form of straps that mate together, with one laying on top of the other. In another embodiment, illustrated, for example, in FIGS. 1B and 2B, a support structure at one end of the gastric band 20 can include an opening through which the other end of the gastric band 20 can feed through to secure the ends to one another. The gastric band 20 can also include a variable volume member, such as an inflatable balloon 24, that is disposed or formed on one side of the support structure 22 and that is configured to be positioned adjacent to tissue. The balloon 24 can expand or contract against the outer wall of the stomach to form an adjustable stoma for controllably restricting food intake into the stomach.

A person skilled in the art will appreciate that the gastric band can have a variety of other configurations. Moreover, the various methods and devices disclosed herein have equal applicability to other types of implantable bands. For example, bands are used for the treatment of fecal incontinence, as described in U.S. Pat. No. 6,461,292 which is hereby incorporated by reference. Bands can also be used to treat urinary incontinence, as described in U.S. Publication No. 2003/0105385 which is hereby incorporated by reference. Bands can also be used to treat heartburn and/or acid reflux, as disclosed in U.S. Pat. No. 6,470,892 which is hereby incorporated by reference. Bands can also be used to treat impotence, as described in U.S. Publication No. 2003/0114729 which is hereby incorporated by reference.

Figure 2B:
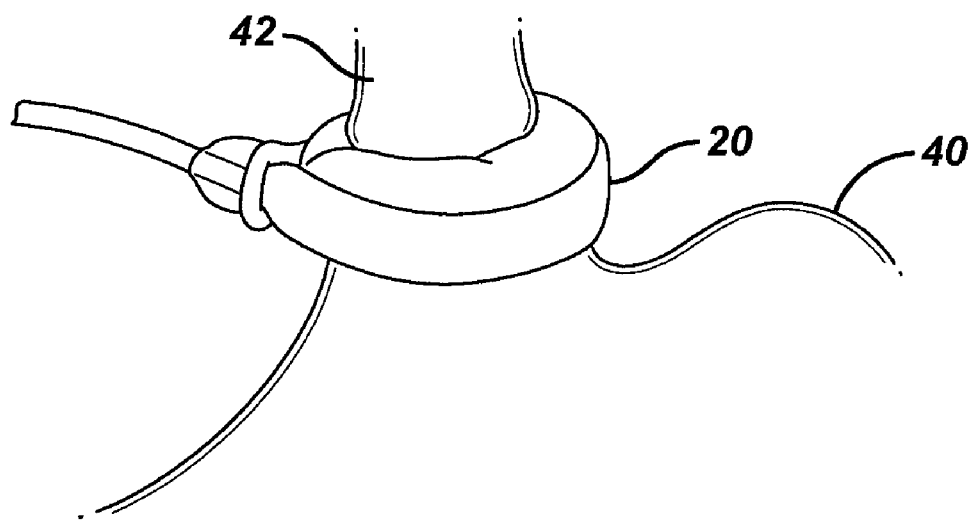
FIG. 2B is a perspective view of the gastric band shown in FIG. 2A as applied to the gastro-esophageal junction of a patient.

FIG. 2B shows the adjustable gastric band 20 applied about the gastro-esophageal junction of a patient. As shown, the band 20 at least substantially encloses the upper portion of the stomach 40 near the junction with the patient's esophagus 42.

After the band 20 is implanted, preferably in the deflated configuration wherein the band 20 contains little or no fluid, the band 20 can be inflated, e.g., using saline, to decrease the size of the stoma opening. A person skilled in the art will appreciate that various techniques, including mechanical and electrical techniques, can be used to adjust the band 20. FIG. 2B also shows an alternate location of a sensing device 41, disposed in a buckle 43 of the band 20.

Figure 3:
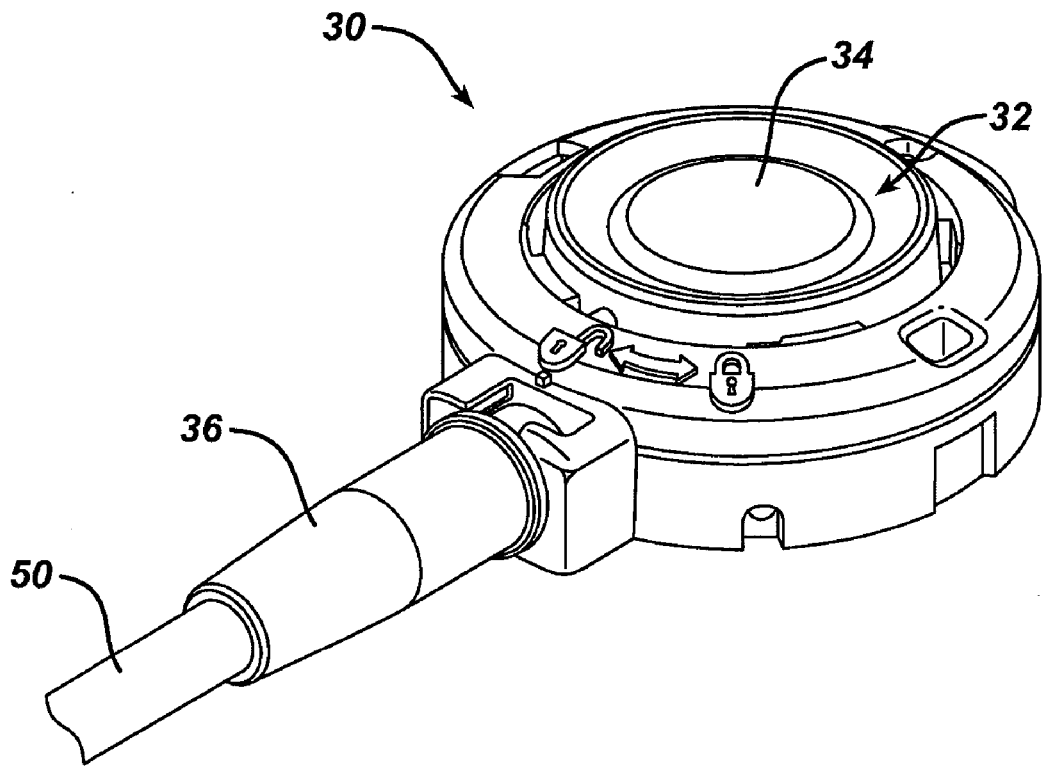
FIG. 3 is a perspective view of the fluid injection port of the restriction system shown in FIG. 1B.

The fluid injection port 30 can also have a variety of configurations. In the embodiment shown in FIG. 3, the injection port 30 has a generally cylindrical housing with a distal or bottom surface and a perimeter wall extending proximally from the bottom surface and defining a proximal opening 32. The proximal opening 32 can include a needle-penetrable septum 34 extending there across and providing access to a fluid reservoir (not visible in FIG. 3) formed within the housing. The septum 34 is preferably placed in a proximal enough position such that the depth of the reservoir is sufficient enough to expose the open tip of a needle, such as a Huber needle, so that fluid transfer can take place. The septum 34 is preferably arranged so that it will self seal after being punctured by a needle and the needle is withdrawn. As further shown in FIG. 3, the port 30 can further include a catheter tube connection member 36 that is in fluid communication with the reservoir and that is configured to couple to a catheter (e.g., the catheter 50). A person skilled in the art will appreciate that the housing can be made from any number of materials, including stainless steel, titanium, or polymeric materials, and the septum 34 can likewise be made from any number of materials, including silicone.

The reading device 70 can also have a variety of configurations, and one exemplary pressure reading device is disclosed in more detail in commonly-owned U.S. Publication No. 2006/0189888 and U.S. Publication No. 2006/0199997, which are hereby incorporated by reference. In general, the reading device 70 can non-invasively measure the pressure of the fluid within the implanted portion 10a even when the pressure sensing device is implanted beneath thick (at least over 10 cm) subcutaneous fat tissue. The physician can hold the reading device 70 against the patient's skin near the location of the sensor housing 60 and/or other pressure sensing device location(s), obtain sensed pressure data and possibly other information as discussed herein, and observe the pressure reading (and/or other data) on a display on the control box 90. The data reading device 70 can also be removably attached to the patient, as discussed further below, such as during a prolonged examination, using straps, adhesives, and other well-known methods. The data reading device 70 can operate through conventional cloth or paper surgical drapes, and can also include a disposal cover (not shown) that may be replaced for each patient.

Figure 4:
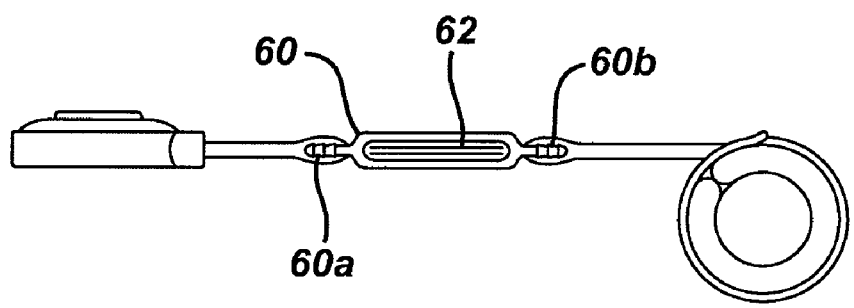
FIG. 4 is a perspective view of another embodiment of a restriction system.

As indicated above, the system 10 can also include one or more sensors for monitoring the operation of the gastric restriction system 10. The sensor(s) can be configured to measure various operational parameters of the system 10 including, but not limited to, a pressure within the system, a temperature within the system, a peristaltic pulse event or frequency, the peristaltic pulse width, the peristaltic pulse duration, and the peristaltic pulse amplitude. In one exemplary embodiment, the system can include a sensor in the form of a pressure measuring device that is in communication with the closed fluid circuit and that is configured to measure the fluid pressure within the system, which corresponds to the amount of restriction applied by the adjustable gastric band to the patient's stomach. In use, measuring the fluid pressure, or any other control parameter of the system, can enable a physician to evaluate the performance of the restriction system. In the illustrated embodiment, shown in FIG. 4, the pressure measuring device is in the form of a pressure sensor 62 disposed within the sensor housing 60. The pressure measuring device can, however, be disposed anywhere within the closed hydraulic circuit of the implantable portion, and various exemplary locations and configurations are disclosed in more detail in commonly-owned U.S. Publication No. 2006/0211913 entitled "Non-Invasive Pressure Measurement In a Fluid Adjustable Restrictive Device," filed on Mar. 7, 2006 and hereby incorporated by reference. In general, the illustrated sensor housing 60 includes an inlet 60a and an outlet 60b that are in fluid communication with the fluid in the implantable portion 10a. An already-implanted catheter 50 can be retrofitted with the sensor housing 60, such as by severing the catheter 50 and inserting barbed connectors (or any other connectors, such as clamps, clips, adhesives, welding, etc.) into the severed ends of the catheter 50. The sensor 62 can be disposed within the housing 60 and be configured to respond to fluid pressure changes within the hydraulic circuit and convert the pressure changes into a usable form of data.

Various pressure sensors known in the art can be used as the pressure sensor 62, such as a wireless pressure sensor provided by CardioMEMS, Inc. of Atlanta, Ga., though a suitable Micro-Electro-Mechanical Systems ("MEMS") pressure sensor may be obtained from any other source, including but not limited to Integrated Sensing Systems, Inc. (ISSYS) of Ypsilanti, Mich. and Remon Medical Technologies, Inc. of Waltham, Mass. One exemplary MEMS pressure sensor is described in U.S. Pat. No. 6,855,115, the disclosure of which is incorporated by reference herein for illustrative purposes only. It will also be appreciated by a person skilled in the art that suitable pressure sensors can include, but are not limited to, capacitive, piezoresistive, silicon strain gauge, or ultrasonic (acoustic) pressure sensors, as well as various other devices capable of measuring pressure.

Figure 5:
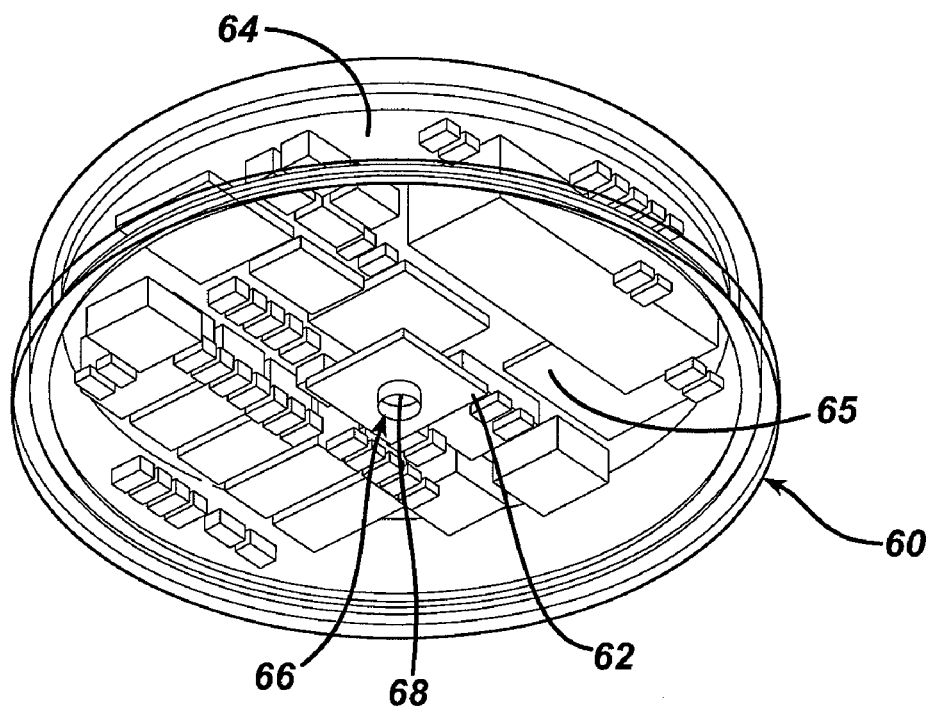
FIG. 5 is a perspective view of the sensor housing shown in FIG. 1A.

One embodiment of a configuration of the sensor housing 60 having the sensor 62 disposed within it is shown in FIG. 5. The sensor housing 60 in this example includes a motherboard that can serve as a hermetic container to prevent fluid from contacting any elements disposed within the sensor housing 60, except as discussed for the sensor 62. The sensor housing 60 can be made from any biocompatible material appropriate for use in a body, such as a polymer, biocompatible metal, and other similar types of material. Furthermore, the sensor housing 60 can be made from any one or more of transparent (as shown in FIG. 5), opaque, semi-opaque, and radio-opaque materials. A circuit board 64 including, among other elements, a microcontroller 65 (e.g., a processor), can also be disposed within the housing 60 to help process and communicate pressure measurements gathered by the sensor 62, and also possibly other data related to the band 20. As further discussed below, the circuit board 64 can also include a transcutaneous energy transfer (TET)/telemetry coil and a capacitor. Optionally, a temperature sensor can be integrated into the circuit board 64. The microcontroller 65, the TET/telemetry coil, the capacitor, and/or the temperature sensor can be in communication via the circuit board 64 or via any other suitable component(s). As described below, the TET/telemetry coil and capacitor can collectively form a tuned tank circuit for receiving power from the external portion 10b and transmitting pressure measurements to a pressure reading device, e.g., the reading device 70. Moreover, to the extent that a telemetry component associated with the pressure sensor 62 is unable to reach a telemetry device external to the patient without some assistance, such assistance can be provided by any suitable number of relays (not shown) or other devices. suitable number of relays (not shown) or other devices.

In use, fluid can enter the sensor housing 60 through an opening 66 located anywhere on the housing's surface (here, the bottom surface) and come into contact with a pressure sensing surface 68 of the sensor 62. The sensor 62 is typically hermetically sealed to the motherboard such that fluid entering the opening 66 cannot infiltrate and affect operation of the sensor 62 except at the pressure sensing surface 68. The sensor 62 can measure the pressure of fluid coming into contact with the pressure sensing surface 68 as fluid flows in and out of the opening 66. For example, the pressure sensing surface 68 can include a diaphragm having a deformable surface such that when fluid flows through the opening 66, the fluid impacts the surface of the diaphragm, causing the surface to mechanically displace. The mechanical displacement of the diaphragm can be converted to an electrical signal by a variable resistance circuit including a pair of variable resistance, silicon strain gauges. One strain gauge can be attached to a center portion of diaphragm to measure the displacement of the diaphragm, while the second, matched strain gauge can be attached near the outer edge of diaphragm. The strain gauges can be attached to the diaphragm with adhesives or can be diffused into the diaphragm structure. As fluid pressure within band 20 fluctuates, the surface of the diaphragm can deform up or down, thereby producing a resistance change in the center strain gauge.

Figure 6:
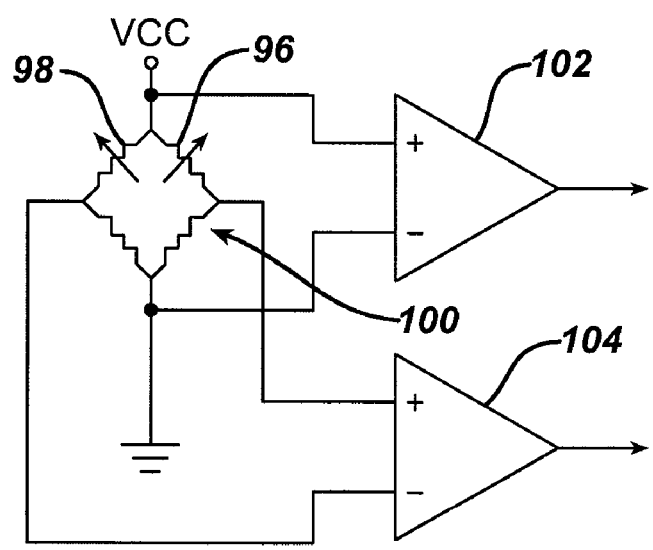
FIG. 6 is a schematic of an embodiment of a variable resistance circuit for the pressure sensor of FIG. 5.

One embodiment of a variable resistance circuit for the sensor 62 is shown in FIG. 6. The circuit includes first and second strain gauges 96, 98 that form the top two resistance elements of a half-compensated, Wheatstone bridge circuit 100. As the first strain gauge 96 reacts to the mechanical displacements of the sensor's diaphragm, the changing resistance of the first gauge 96 changes the potential across the top portion of the bridge circuit 100. The second strain gauge 98 is matched to the first strain gauge 96 and athermalizes the Wheatstone bridge circuit 100. First and second differential amplifiers 102, 104 are connected to the bridge circuit 100 to measure the change in potential within the bridge circuit 100 due to the variable resistance strain gauges 96, 98. In particular, the first differential amplifier 102 measures the voltage across the entire bridge circuit 100, while the second differential amplifier 104 measures the differential voltage across the strain gauge half of bridge circuit 100. The greater the differential between the strain gauge voltages, for a fixed voltage across the bridge, the greater the pressure difference. Output signals from the differential amplifiers 102, 104 can be applied to the microcontroller 65 integrated into the circuit board 64, and the microcontroller 65 can transmit the measured pressure data to a device external to the patient. If desired, a fully compensated Wheatstone bridge circuit can also be used to increase the sensitivity and accuracy of the pressure sensor 62. In a fully compensated bridge circuit, four strain gauges are attached to the surface of diaphragm rather than only two strain gauges.

Figure 7:
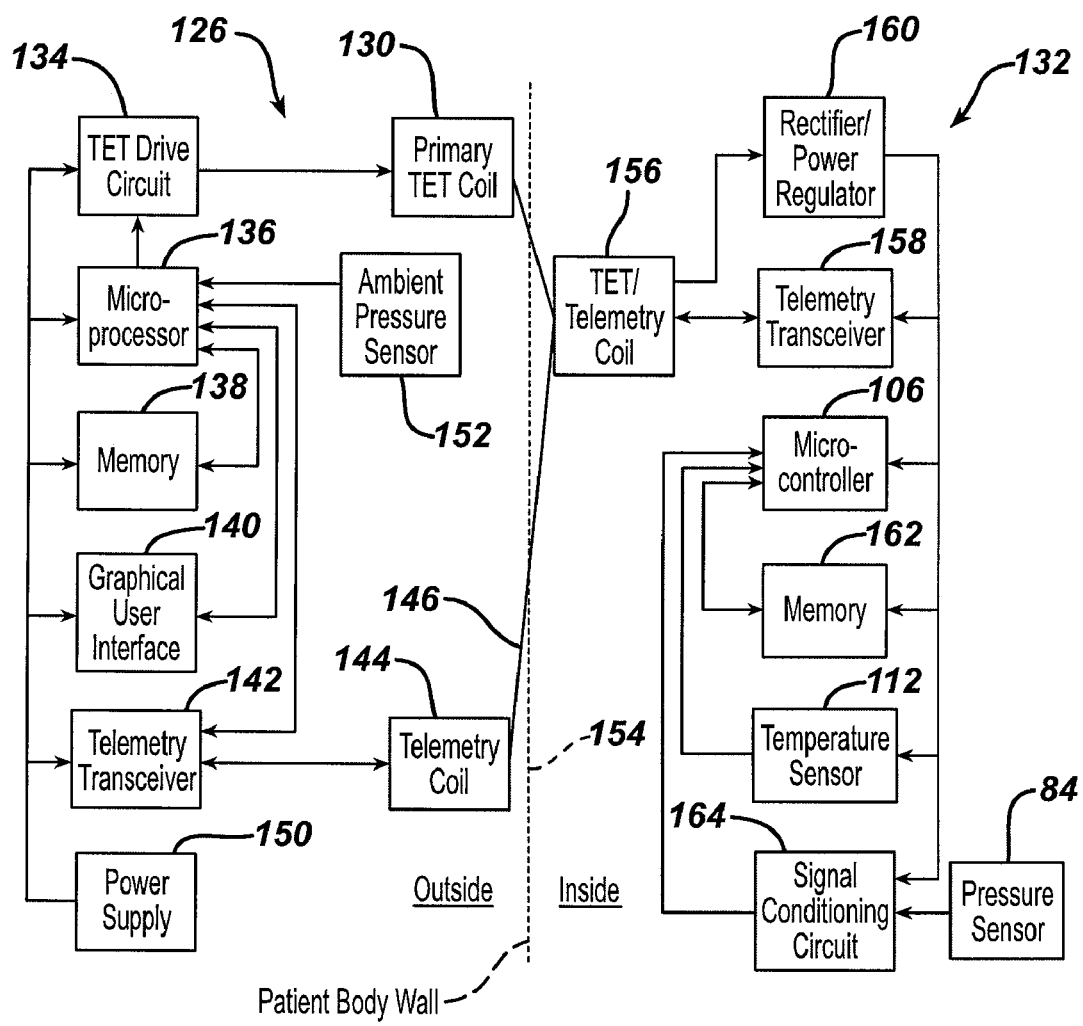
FIG. 7 is a block diagram of one embodiment of a pressure management system for use in conjunction with the restriction system shown in FIG. 4.

FIG. 7 illustrates one embodiment of components included in the internal and external portions 10*a*, 10*b*. As shown in FIG. 7, the external portion 10*b* includes a primary TET coil 130 for transmitting a power signal to the internal portion 10*a*. A telemetry coil 144 is also included for transmitting data signals to the internal portion 10*a*. The primary TET coil 130 and the telemetry coil 144 combine to form an external antenna, e.g., the reading device 70. The external portion 10*b*, e.g., disposed in the control box 90, can include a TET drive circuit 134 for controlling the application of power to the primary TET coil 130. The TET drive circuit 134 is controlled by a microprocessor 136 having an associated memory 138. A graphical user interface 140 is connected to the microprocessor 136 for inputting patient information, displaying data and physician instructions, and/or printing data and physician instructions. Through the user interface 140, a user such as the patient or a clinician can transmit an adjustment request to the physician and can also enter reasons for the request. Additionally, the user interface 140 can enable the patient to read and respond to instructions from the physician and/or pressure measurement alerts.

The external portion 10*b* can also include a primary telemetry transceiver 142 for transmitting interrogation commands to and receiving response data, including sensed pressure data, from the implanted microcontroller 65. The primary transceiver 142 is electrically connected to the microprocessor 136 for inputting and receiving command and data signals. The primary transceiver 142 drives the telemetry coil 144 to resonate at a selected RF communication frequency. The resonating circuit can generate a downlink alternating magnetic field 146 that transmits command data to the microcontroller 65. Alternatively, the transceiver 142 can receive telemetry signals transmitted from a secondary TET/telemetry coil 156 ("the internal antenna") in the internal portion 10*a*. The received data can be stored in the memory 138 associated with the microprocessor 136. A power supply 150 can supply energy to the control box 90 in order to power element(s) in the internal portion 10*a*. An ambient pressure sensor 152 is connected to microprocessor 136. The microprocessor 136 can use a signal from the ambient pressure sensor 152 to adjust the received pressure measurements for variations in atmospheric pressure due to, for example, variations in barometric conditions or altitude, in order to increase the accuracy of pressure measurements.

FIG. 7 also illustrates components of the internal portion 10*a*, which in this embodiment are included in the sensor housing 60 (e.g., on the circuit board 64). As shown in FIG. 7, the secondary TET/telemetry coil 114 receives the power/communication signal 132 from the external antenna. The secondary coil 114 forms a tuned tank circuit that is inductively coupled with either the primary TET coil 130 to power the implant or the primary telemetry coil 144 to receive and transmit data. A telemetry transceiver 158 controls data exchange with the secondary coil 114. Additionally, the internal portion 10*a* includes a rectifier/power regulator 160, the microcontroller 65, a memory 162 associated with the microcontroller 65, a temperature sensor 112, the pressure sensor 62, and a signal conditioning circuit 164. The implanted components can transmit pressure measurements (with or without adjustments due to temperature, etc.) from the sensor 62 to the control box 90 via the antenna (the primary TET coil 130 and the telemetry coil 144). Pressure measurements can be stored in the memory 138, adjusted for ambient pressure, shown on a display on the control box 90, and/or transmitted, possibly in real time, to a remote monitoring station at a location remote from the patient.

As indicated above, the internal circuitry, or at least some portion thereof, can be fabricated and/or designed so as to be hardened against the effects of radiation. Radiation hardening is a method of designing and testing electronic components and systems to make them resistant to damage or malfunctions caused by high-energy subatomic particles and electromagnetic radiation. As known to those skilled in the art, radiation can have a wide range of adverse effects on electrical circuitry. Such effects can be cumulative over the course of multiple applications of radiation (i.e., Total Ionizing Dose) or such effects can result from a one-time application of such energy (i.e., Single-Event Effects). In either case, such effects can corrupt the internal circuitry resulting in inefficient processing of data and/or failure of the system. As presently provided, the internal circuitry can be hardened against the effect(s) of some pre-determined dose, type, and/or amount of radiation being applied to the device so as to provide some desired therapeutic effect (e.g., sterilization of the device). In an exemplary embodiment, the internal circuitry is fabricated and/or designed so that the circuitry and thus the functionality of the device itself, can withstand an amount of radiation in the range of up to about 100 kGy (including a single dose in the range of about 25 kGy to about 50 kGy). In some embodiments, the internal circuitry can be fabricated so as to withstand multiple doses of radiation in the range of about 25 kGy to about 50 kGy (up to about 100 kGy or higher, if desired). Examples of the internal circuitry that can be fabricated, configured, and/or manufactured so as to withstand such radiation include a circuit board, an integrated circuit (e.g., an application specific integrated circuit), a gate array, a surface acoustical wave ("SAW") device, a magnetic control circuit, a sensor, a microprocessor, a microcontroller, a memory device, signal conditioning circuitry, etc.

The internal circuitry can be radiation hardened in various manners. For example, the circuitry can be fabricated at least in part from any of a number of radiation compliant materials. Examples of such materials include ceramic materials, titanium, gold, silver, tantalum, platinum, palladium, rhodium, etc. Various other such materials will be apparent to those skilled in the art. In an exemplary embodiment, the internal circuitry, or at least some portion thereof, can be fabricated utilizing silicon-on-insulator ("SOI") technology. SOI technology refers to the use of a layered silicon-insulator-silicon substrate in place of conventional silicon substrates in semiconductor manufacturing, especially microelectronics, to reduce parasitic device capacitance and thereby improve performance. SOI-based devices differ from conventional silicon-built devices in that the silicon junction is above an electrical insulator, typically sapphire or silicon dioxide. The choice of insulator depends largely on intended application, with sapphire being used for radiation-sensitive applications and silicon oxide typically being used for improved performance and diminished short channel effects in microelectronics devices. The precise thickness of the insulating layer and topmost silicon layer can also vary widely with application, as one skilled in the art will appreciate.

Figure 8A:
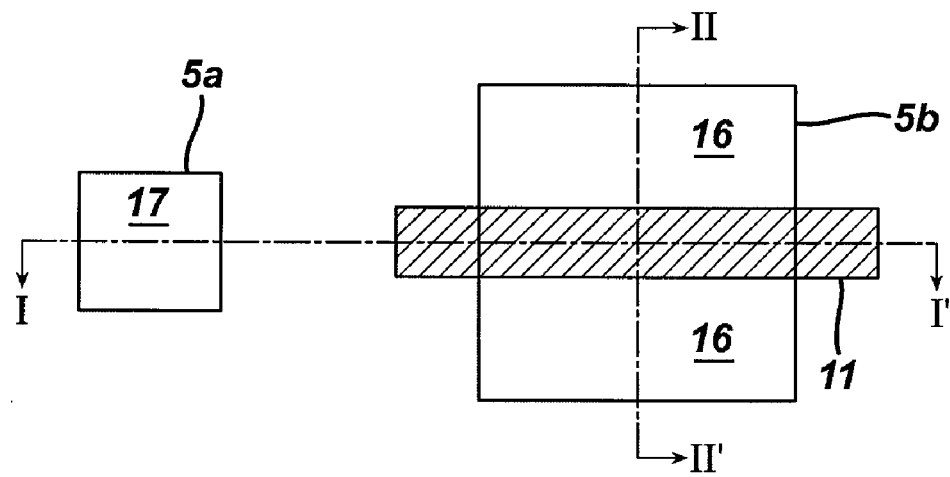
FIG. 8A is a representation of an integrated circuit fabricated utilizing silicon-on-insulator technology.
Figure 8B:
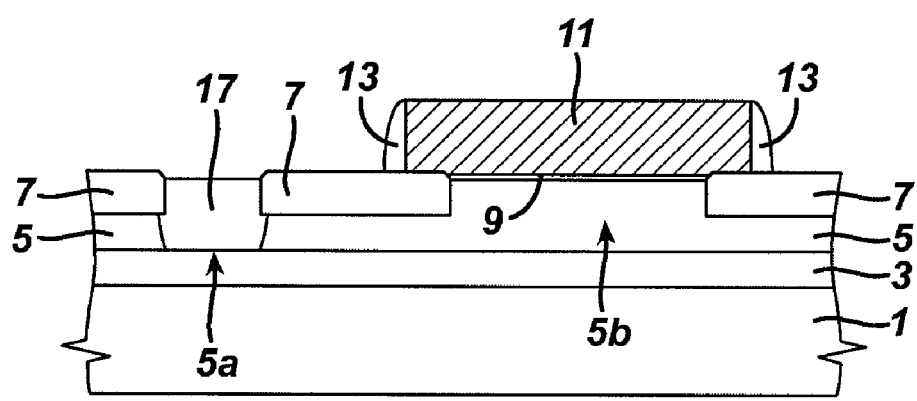
FIG. 8B is a cross-sectional view of the integrated circuit of FIG. 8A.
Figure 8C:
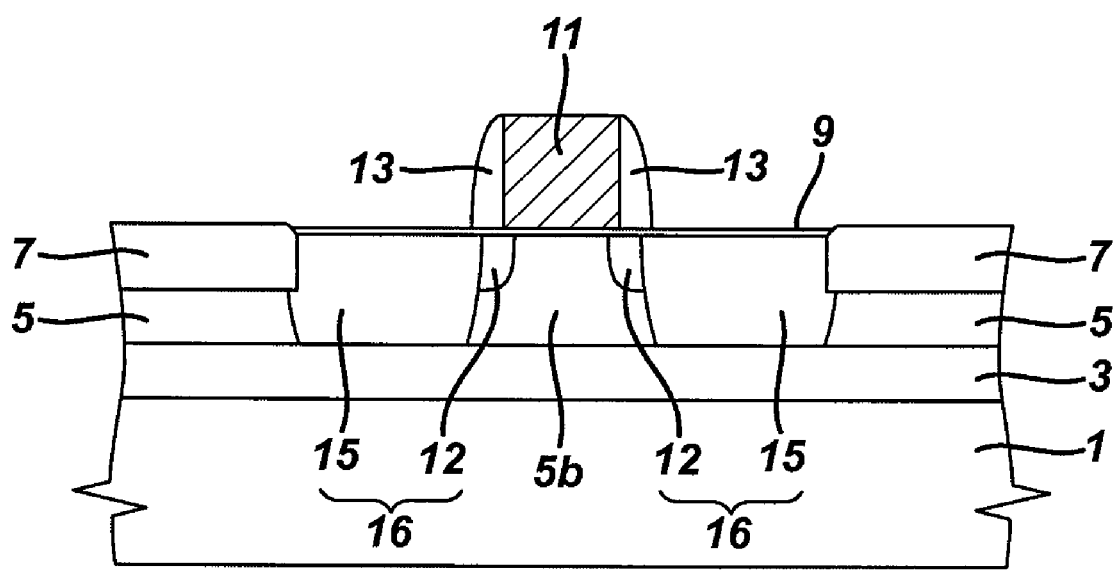
FIG. 8C is another cross-sectional view of the integrated circuit of FIG. 8A.

FIGS. 8A-8C provide an example of an integrated circuit fabricated via SOI technology. FIG. 8A is a top plan view schematically showing a conventional SOI transistor. Also, FIG. 8B is a cross-sectional view taken along the line I-I' of FIG. 8A, and FIG. 8C is a cross-sectional view taken along the line II-II of FIG. 8A. As shown, an SOI structure typically includes a supporting substrate 1, a buried insulating layer 3 on the supporting substrate 1 and a semiconductor layer 5 of a first conductivity type on the buried insulating layer 3. The semiconductor layer 5 can be etched to form a partial trench region having a depth which is less than the thickness of the semiconductor layer 5. Thus, a semiconductor residue layer exists under the partial trench region. The partial trench region defines a transistor active region 5b and a body contact active region 5a spaced apart from the transistor active region 5b. The partial trench region is then filled with an isolation layer 7. An insulated gate pattern 11 crosses over the transistor active region 5b. The insulated gate pattern 11 is electrically isolated from the transistor active region 5b by a gate dielectric layer 9. Source/drain regions 16 of a second conductivity type are formed at the transistor active region 5b, which is located at both sides of the insulated gate pattern 11.

Each of the source/drain regions 16 may have a lightly doped drain (LDD) structure. This LDD structure comprises a lightly doped region 12 and a heavily doped region 15, and may be realized using a spacer 13 formed on the sidewall of the insulated gate pattern 11. Here, the source/drain regions 16 are formed so that they are in contact with the buried insulating layer 3 in order to reduce parasitic capacitance. Impurities of the first conductivity type are implanted into the body contact active region 5a, thereby forming a well contact region 17 at the body contact active region 5a.

Figure 9A:
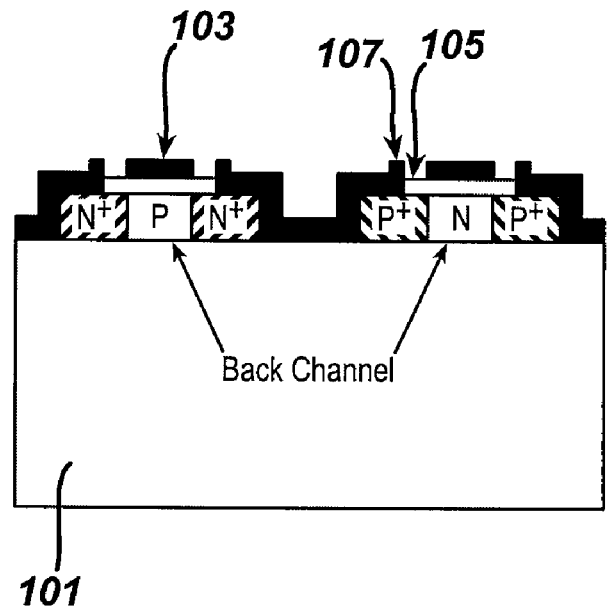
FIG. 9A is a cross-sectional view of another embodiment of an integrated circuit fabricated utilizing silicon-on-insulator technology.
Figure 9B:
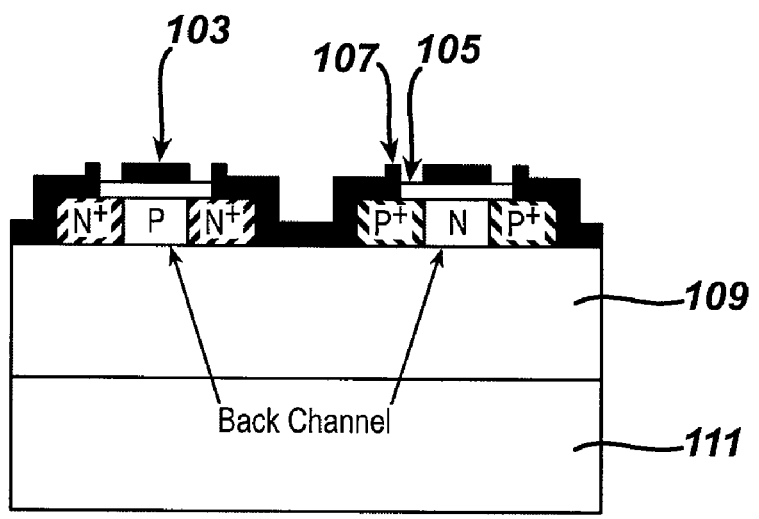
FIG. 9B is a cross-sectional view of yet another embodiment of an integrated circuit fabricated utilizing silicon-on-insulator technology.

FIGS. 9A and 9B provide alternative embodiments of such SOI hardened circuitry. For example, FIG. 9A shows a cross-sectional view of an integrated circuit having a thin layer of silicon 107 disposed on a sapphire substrate 101. Additionally, the circuitry includes a gate element comprising a metal 103 and an underlying oxide 105. Alternatively, FIG. 9B shows an integrated circuit formed by an insulator layer 109 fabricated from, for example, silicon dioxide being disposed on a silicon substrate 111. Further, like in FIG. 9A, the circuitry further includes a thin layer of silicon 107 being disposed on the insulator layer 109. As will be appreciated by those skilled in the art, the identity and/or thickness of each layer can be specifically designed so as to provide the desired functionality and/or radiation hardening.

SOI offers many inherent advantages capable of mitigating or eliminating both Total Ionizing Dose effects and Single-Event Effects. For instance, SOI inherently eliminate latchup. A latchup is the inadvertent creation, which can result from the introduction of a sterilization radiation, of a low-impedence path between the power supply rails of an electronic component, triggering a parasitic structure, which then acts as a short-circuit, disrupting proper functioning of the part and possibly even leading to its destruction due to overcurrent. The SOI design eliminates the possiblitiy of a latch-up by providing the layer of insulating oxide (called a "trench") around, for example, both N-metal-oxide semiconductor ("NMOS") and P-metal-oxide semiconductor ("PMOS") transistors. This breaks the parasitic structure between these transistors.

Additionally, the internal circuitry can utilize gallium arsenide ("GaAs") technology. GaAs has been known to exhibit various properties superior to that of silicon (e.g., ability to withstand radiation) in semiconductor performance. Thus, GaAs technology can be utilized, for example, in such components as memory devices, solar devices, solar cells, and field effect transistors ("FETs"). As indicated, GaAs has some electronic properties which are superior to that of silicon. For example, GaAs has a higher saturated electron velocity and higher electron mobility, allowing transistors made from GaAs to function at frequencies in excess of about 250 GHz. Also, GaAs devices generate less noise than silicon devices when operated at high frequencies. GaAs devices can also be operated at higher power levels than the equivalent silicon device because they have higher breakdown voltages.

In addition to fabricating various portions of the internal circuity so as to withstand a pre-determined dose of sterilization radiation, the internal circuitry can include any number and/or type of component(s) which are inherently radiation resistant. For example, the internal circuitry can utilize magnetic field based technology which can be configured to withstand desired amounts of radiation. Various embodiments of such magnetic field based technologies are within the spirit and scope of the present disclosure. Such embodiments can include the use of Magnetoresistive Random Access Memory ("MRAM"), magnetic reed switches utilizing a magnetic field to open and close the switch, Hall Effect devices, and inductively coupled power supply circuits which include magnetic coils, rectifiers and power regulation circuitry.

Referring again to Magnetoresistive Random Access Memory, MRAM is a non-volatile computer memory (NVRAM) technology which is known to be inherently radiation resistant. Unlike conventional RAM chip technologies, in MRAM data is not stored as electric charge or current flows, but by magnetic storage elements. As shown in FIG. 10A, the elements are formed from two ferromagnetic plates 117, 121, each of which can hold a magnetic field, separated by a thin insulating layer 119. One of the two plates is a permanent magnet 121 set to a particular polarity, the other plate's 117 field will change to match that of an external field. A memory device is built from a grid of such "cells."

Reading is accomplished by measuring the electrical resistance of the cell. A particular cell is (typically) selected by powering an associated transistor which switches current from a supply line through the cell to ground. Due to the magnetic tunnel effect, the electrical resistance of the cell changes due to the orientation of the fields in the two plates 117, 121. By measuring the resulting current, the resistance inside any particular cell can be determined, and from this the polarity of the writable plate. Typically if the two plates have the same polarity this is considered to mean "0," while if the two plates are of opposite polarity the resistance will be higher and this means "1."

Figure 10B:
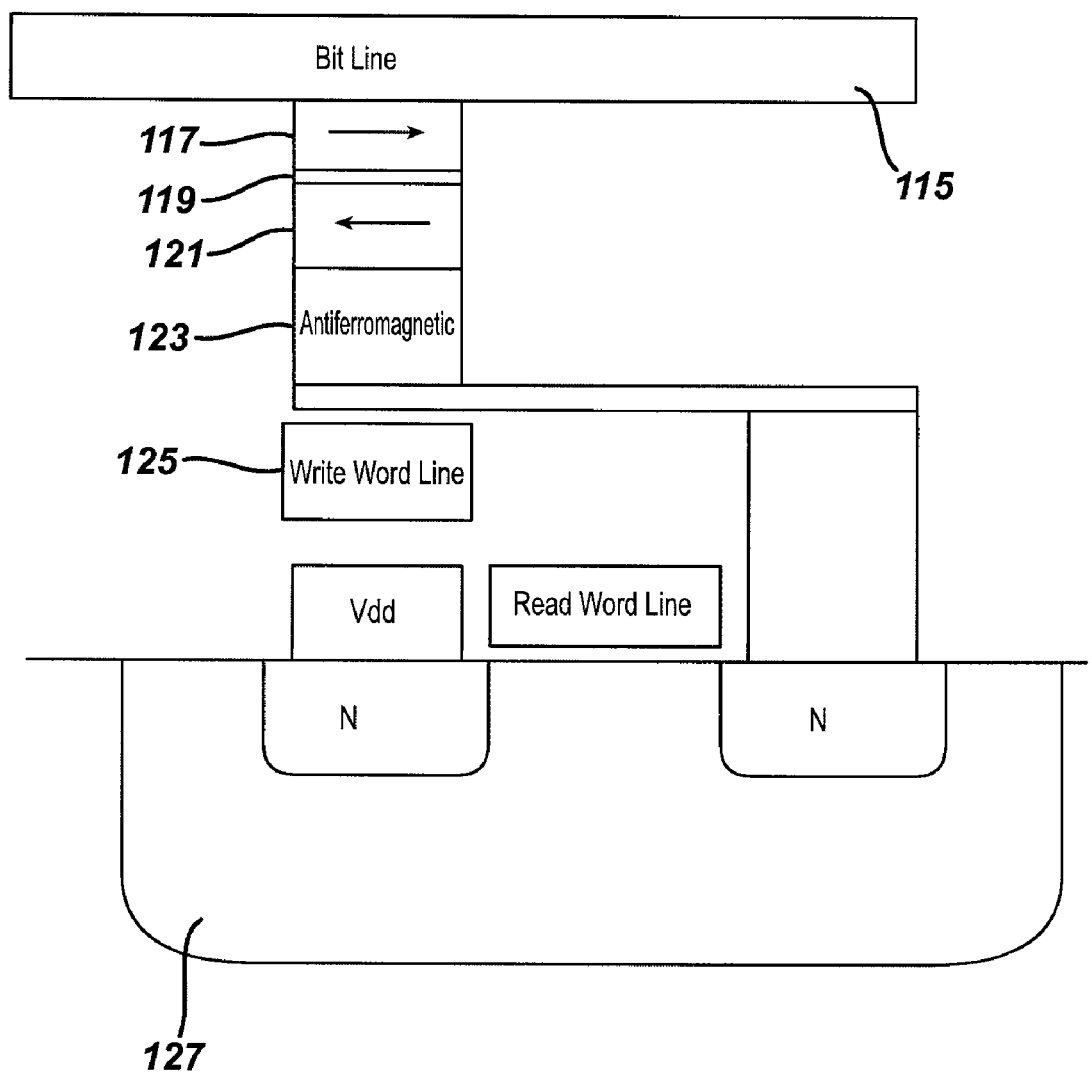
FIG. 10B is a cross-sectional view of an MRAM component incorporated into an integrated circuit.

Data is written to the cells using a variety of means. For example, in one embodiment each cell lies between a pair of write lines 115, 125 arranged at right angles to each other, above and below the cell. When current is passed through them 115, 125, an induced magnetic field is created at the junction, which the writable plate picks up. FIG. 10B provides an example of the MRAM circuitry being incorporated into a silicon (or SOI) substrate 127. Again, those skilled in the art will understand that these representations are merely examples and the circuitry can include a wide range of architecture and/or components capable of withstanding the desired sterilization procedure.

Another example of a radiation hardened device is a Surface Acoustic Wave ("SAW") device such as a radio-frequency identification ("RFID") tag. SAW devices inherently withstand elevated operating temperatures, high energy x-rays, and/or gamma sterilization radiation. In an exemplary embodiment, the SAW RFID tag (commercially available from RF SAW, Inc.; Richardson, Tex.) operates on a piezoelectric effect and communicates preprogrammed data from the device by sending acoustic wave pulses that are reflected back to a reader unit. SAW devices are also commonly used as electrical wave pulses that are reflected back to a reader unit. Additionally, SAW devices can be used as electrical noise filters due to their slow propagation time. For example, the SAW device could be a band-pass filter as well as other types of RF filters that will be obvious to those skilled in the art.

In addition to the systems and devices described above, a method for sterilizing an implantable medical device is provided. Like above, various types of implantable medical devices can be utilized with the presently disclosed method. For example, the implantable device can be configured to be disposed within a patient's peritoneal cavity. In an exemplary embodiment, the method includes providing an implantable restriction device which is configured to form a restriction in a pathway. Similar to above, the implantable medical device can include an internal control module with electronic components configured to be resistant to a pre-determined dose of radiation. Examples of the electronic components that can be fabricated, configured, and/or manufactured in this manner include a circuit board, an integrated circuit (e.g., an application specific integrated circuit), a gate array, a surface acoustical wave device, a magnetic control circuit, a sensor, a microprocessor, a microcontroller, a memory device, signal conditioning circuitry, etc. The method can also include delivering a pre-determined dose of radiation to the implantable medical device.

The internal components can be configured in any manner capable of providing the desired radiation resistance. For example, the electronic component(s) can be fabricated at least in part from a radiation compliant material (e.g., a ceramic material, titanium, gold, silver, tantalum, platinum, palladium, rhodium, etc.). Additionally, the electronic components can be fabricated at least in part utilizing gallium arsenide technology. Also, at least some portion of the internal circuitry can be fabricated utilizing SOI technology. Further, the internal circuitry can include various components which are inherently resistant to radiation. Like above, such components can include SAW devices and/or various devices fabricated utilizing magnetic field based technology (e.g., MRAM).

The internal circuitry can be fabricated and/or designed so as to be resistant to any degree, dosage, type, and/or amount of radiation as desired to provide the desired sterilization. For example, the radiation can be gamma radiation, x-ray radiation, electron beam radiation, etc. Also, the radiation dose (single dose or cumulative) can be any amount as desired to provide the desired sterilization. For example, in an exemplary embodiment the total dosage can be up to about 100 kGy (including single doses in the range of about 25 kGy to about 50 kGy). In some embodiments, the sterilization regimen can include delivering at least one additional dose of a pre-determined amount of radiation. As will be appreciated by those skilled in the art, any amount of sterilization radiation delivered as a single dose or multiple doses is within the spirit and scope of the presently disclosed method.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A method for sterilizing an implantable medical device, comprising:

providing an implantable medical device configured to be disposed within a patient's peritoneal cavity, the implantable medical device in electrical communication with an internal control module having any number of electronic components configured to be resistant to a pre-determined dose of radiation, at least one of the electronic components comprising a magnetoresistive random access memory (MRAM), at least one of the electronic components being configured to sense a fluid pressure within the implantable medical device; and delivering a pre-determined dose of radiation to the implantable medical device.

2. The method of claim 1, wherein the implantable medical device is a restriction device configured to form a restriction in a pathway.

3. The method of claim 1, wherein at least one of the electronic components are fabricated utilizing silicon-on-insulator technology.

4. The method of claim 1, wherein the radiation is selected from the group consisting of gamma radiation, x-ray radiation, and electron beam radiation.

5. The method of claim 1, wherein the pre-determined dose of radiation is any amount up to about 100 kGy.

6. The method of claim 1, further comprising delivering at least one additional dose of a pre-determined amount of radiation.

7. A method for sterilizing an implantable medical device, comprising:

providing an implantable medical device having located therein, any number of electronic components configured for controlling the implantable medical device, at least one of the electronic components comprising a magnetoresistive random access memory (MRAM), wherein at least one of the electronic components is fabricated using silicon-on-insulator technology with a sapphire insulator; and delivering radiation to the implantable medical device to sterilize the implantable medical device.

8. The method of claim 7, wherein the implantable medical device is a restriction device configured to form a restriction in a pathway.

9. The method of claim 7, wherein the radiation is delivered in a pre-determined dose up to about 100 kGy.

10. The method of claim 7, wherein the radiation is selected from the group consisting of gamma radiation, x-ray radiation, and electron beam radiation.

11. A method for sterilizing an implantable medical device, comprising:

providing an implantable medical device having located therein, any number of electronic components configured for controlling the implantable medical device, at least one of the electronic components comprising a magnetoresistive random access memory (MRAM), wherein at least one of the electronic components is fabricated using silicon-on-insulator technology with a silicon dioxide insulator; and delivering radiation to the implantable medical device to sterilize the implantable medical device.

12. The method of claim 11, wherein the implantable medical device is a restriction device configured to form a restriction in a pathway.

13. The method of claim 11, wherein the radiation is delivered in a pre-determined dose up to about 100 kGy.

* * * * *